(12) United States Patent
Banks

(10) Patent No.: US 6,255,333 B1
(45) Date of Patent: *Jul. 3, 2001

(54) PARASITICIDAL COMPOUNDS

(75) Inventor: Bernard Joseph Banks, Sandwich (GB)

(73) Assignee: Pfizer Inc., New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,815
(22) PCT Filed: Aug. 5, 1996
(86) PCT No.: PCT/EP96/03501
§ 371 Date: Feb. 11, 1998
§ 102(e) Date: Feb. 11, 1998
(87) PCT Pub. No.: WO97/07102
PCT Pub. Date: Feb. 27, 1997

(30) Foreign Application Priority Data

Aug. 11, 1995 (GB) .................................................. 9516454
Jan. 19, 1996 (GB) .................................................. 9601128

(51) Int. Cl.⁷ .................. A61K 31/415; A61P 33/00; C07P 231/12
(52) U.S. Cl. .................. 514/406; 548/110; 548/364.1; 548/365.7; 548/370.1; 548/371.7; 548/372.5; 548/374.1; 548/375.1; 548/376.1; 548/377.1
(58) Field of Search .................. 548/377.1, 375.1, 548/376.1

(56) References Cited

U.S. PATENT DOCUMENTS 5,091,378   2/1992  Karanewsky et al. .
5,608,077 * 3/1997  Hatton et al. ...................... 548/365.1

FOREIGN PATENT DOCUMENTS 0658547     6/1995  (EP) .
WO 87/03781 7/1987  (WO) .

OTHER PUBLICATIONS

Nishino et al., Journal of Heterocyclic Chemistry; vol. 33, No. (4), pp. 1291–1302, (1996).
Chemical Abstracts, American Chemical Society; vol. 125, No. (3), p. 33544, (1996).

(List continued on next page.)

*Primary Examiner*—Robert W. Ramsuer
(74) *Attorney, Agent, or Firm*—Peter C. Richardson; Gregg C. Benson; B. Timothy Creagan

(57) ABSTRACT

Parasiticidal pyrazole derivatives of formula (I) wherein: $R^1$ represents CN, $C_{1-6}$ alkoxycarbonyl, $NO_2$, CHO, $C_{1-6}$ alkanoyl, phenyl optionally substituted by one or more halogen, or $C_{1-6}$ alkyl optionally substituted by one or more halogen; $R^2$ represents a group of formula (II), (III) or (IV) in which: $R^7$ represents H, halogen, carbamoyl, cyano, tri($C_{1-6}$ alkyl)silyl, $C_{1-6}$ alkyl (optionally substituted by one or more halogen, OH or $C_{1-6}$ alkoxy), $C_{1-6}$ alkoxycarbonyl, phenyl, or a 5- or 6-membered ring heterocycle which is saturated or partially or fully unsaturated and contains up to 4 hetero-atoms independently selected from up to 4 N atoms, up to 2 O atoms and up to 2 S atoms and which is attached to the alkynyl moiety by an available C, S or N atom where the valence allows; and $R^8$, $R^9$ and $R^{10}$ each independently represents H, halogen, phenyl optionally substituted by one or more halogen, CN or $C_{1-6}$ alkyl optionally substituted by one or more halogen; $R^3$ represents H, $C_{1-6}$ alkyl, halogen, $NH_2$, $NH(C_{1-6}$ alkanoyl), $NH(C_{1-6}$ alkoxycarbonyl), $N(C_{1-6}$ alkoxycarbony)$_2$, $NH(C_{1-6}$ alkyl), $N(C_{1-6}$ alkyl)$_2$, NHCONH($C_{1-6}$ alkyl), N-pyrrolyl, NHCONH(phenyl optionally substituted by one or more halogen), N—CH(phenyl), OH, $C_{1-6}$ alkoxy, SH or $S(O)_n(C_{1-6}$ alkyl optionally substituted by one or more halogen) where n is 0, 1 or 2; and $R^4$, $R^5$ and $R^6$ each independently represents H, halogen, $C_{1-6}$ alkyl optionally substituted by one or more halogen, $C_{1-6}$ alkoxy optionally substituted by one or more halogen, $S(O)_n(C_{1-6}$ alkyl optionally substituted by one or more halogen) where n is 0, 1 or 2, or $CH_3CO$, CN, $CONH_2$, $CSNH_2$, $OCF_3$, $SCF_3$ or $SF_5$; or a pharmaceutically or veterinarily acceptable salt thereof.

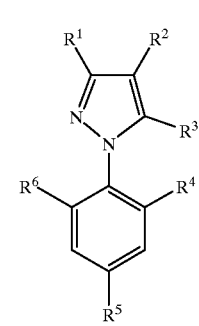

(I)

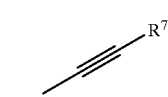

(II)

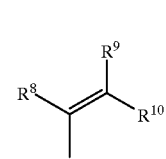

(III)

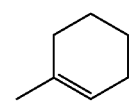

(IV)

17 Claims, No Drawings

OTHER PUBLICATIONS

Gunnel Westoo, Acta Chemica Scandinavica; vol. 13, pp. 683–688, (1959).
Chemical Abstracts, American Chemical Society; vol. 75, No. (1), p. 5057 (1971).
Synthesis, International Journal of Methods in Synthesis Oganic Chemistry; vol. 12, pp. 1052–1054, (1984).
Junek et al., Chem. Ber.; vol. 106, pp. 914–921, (1973).
Chemical Abstracts, American Chemical Society; vol. 108, No. (15), pp. 741–742, (1988).
Chemical Abstracts, American Chemical Society; vol. 116, No. (25), pp. 782, (1992).
Journal of The Chemical Society; pp. 1112–1116, (1974).
Journal of the Chemical Society; pp. 2008–2012, (1973).
H. H. Otto, et al., Monatshette fur Chemie; vol. 111, pp. 53–61, (1980).
Simon, Mercedes Medio, New Cycloaddition Reactions of 1–Phenyl–4–Vinylpyrazole, Dec. 1986.*

* cited by examiner

PARASITICIDAL COMPOUNDS

This application is the United States National filing of International Patent Application PCT/EP96/03501, which was a continuation of Great Britain Patent Applications 9516454.7 and 9601128.3, filed Aug. 11, 1995 and Jan. 19, 1996, respectively, now abandoned.

This invention relates to pyrazole derivatives having parasiticidal properties.

Certain parasiticidal pyrazole derivatives are already known. These include fipronil (5-amino-3-cyano-1-(2,6-dichloro-4-trifluoromethylphenyl)-4-trifluoromethylsulphinyl-pyrazole) and certain analogues thereof mentioned in International Patent Application WO 87/03781.

EP 0 658 547 A1 discloses a number of 4-alkenyl and 4-alkynyl pyrazoles with H and alkyl at the 1-position, and a carbamate group at position 5 of the pyrazole, as antifungal agents.

A new group of parasiticidal pyrazole derivatives has now been found. Thus, according to the present invention, there is provided a compound of formula I,

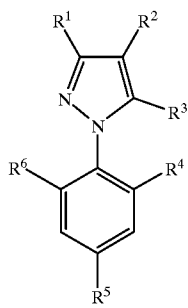

I wherein $R^1$ represents CN, $C_{1-6}$ alkoxycarbonyl, $NO_2$, CHO, $C_{1-6}$ alkanoyl, phenyl optionally substituted by one or more halogen, or $C_{1-6}$ alkyl optionally substituted by one or more halogen;

$R^2$ represents a group of formula II, III or IV,

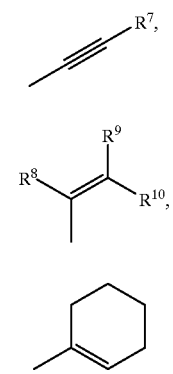

II

III

IV in which $R^7$ represents H, halogen, carbamoyl cyano, tri($C_{1-6}$ alkyl)silyl, $C_{1-6}$ alkyl (optionally substituted by one or more halogen, OH or $C_{1-6}$ alkoxy), $C_{1-6}$ alkoxycarbonyl, phenyl, or a 5- or 6-membered ring heterocycle which is saturated or partially or fully unsaturated and contains up to 4 hetero-atoms independently selected from up to 4 N atoms, up to 2 O atoms and up to 2 S atoms and which is attached to the alkynyl moiety by an available C, S or N atom where the valence allows; and and $R^8$, $R^9$ and $R^{10}$ each independently represent H, halogen, phenyl optionally substituted by one or more halogen, CN or $C_{1-6}$ alkyl optionally substituted by one or more halogen;

$R^3$ represents H, $C_{1-6}$ alkyl halogen, $NH_2$, $NH(C_{1-6}$ alkanoyl), $NH(C_{1-6}$ alkoxycarbonyl), $N(C_{1-6}$ alkoxycarbonyl)$_2$, $NH(C_{1-6}$ alkyl), $N(C_{1-6}$ alkyl)$_2$, NHCONH($C_{1-6}$ alkyl), N-pyrrolyl, NHCONH(phenyl optionally substituted by one or more halogen), N=CH (phenyl), OH, $C_{1-6}$ alkoxy, SH or $S(O)_n(C_{1-6}$ alkyl optionally substituted by one or more halogen) where n is 0,1 or 2; and $R^4$, $R^5$ and $R^6$ each independently represent H, halogen, $C_{,4}$ alkyl optionally substituted by one or more halogen, $C_{1-6}$ alkoxy optionally substituted by one or more halogen, $S(O)_n(C_{1-6}$ alkyl optionally substituted by one or more halogen) where n is 0,1 or 2, or $CH_3CO$, CN, $CONH_2$, $CSNH_2$, $OCF_3$, $SCF_3$ or $SF_5$;

or a pharmaceutically or veterinarily acceptable salt thereof (hereinafter referred to together as "the compounds of the invention").

Alkyl groups may be straight, cyclic or branched, where the number of carbon atoms allows. Halogen means fluoro, chloro, bromo or iodo.

Pharmaceutically and veterinarily acceptable addition salts are well known to those skilled in the art, and for example include those mentioned by Berge et al in *J.Pharm. Sci.*, 66,1–19 (1977).

$R^1$ is preferably CN, optionally substituted phenyl, optionally substituted $C_{1-6}$ alkyl, or $C_{1-6}$ alkoxycarbonyl.

$R^1$ is more preferably CN, Ph, $CO_2C_2H_5$, $CH_3$, $CF_3$ or $CO_2CH_3$.

$R^2$ is preferably a group of formula II where $R^7$ is H, tri($C_{1-6}$ alkyl)silyl, $C_{1-6}$ alkyl optionally substituted by one or more halogen, OH or $C_{1-6}$ alkoxy, or $R^7$ is $C_{1-6}$ alkoxycarbonyl phenyl a 5- or 6-membered zing heterocycle as previously defined, halogen, or a group of formula III in which $R^8$, $R^9$, and $R^{10}$ are each H, or a group of formula III in which two of $R^8$, $R^9$ and $R^{10}$ are halogen and the other is H, CN, phenyl optionally substituted by one or more halogen or $C_{1-6}$ alkyl optionally substituted by one or more halogen, or a group of formula III in which $R^8$, $R^9$ and $R^{10}$ are each independently F, Cl, Br or I, or a group of formula III in which $R^8$ is H or $C_{1-6}$ alkyl optionally substituted by one or more halogen, OH or $C_{1-6}$ alkoxy, and $R^9$ and $R^{10}$ are both halogen, or a group of formula III in which $R^8$ is H and one of $R^9$ and $R^{10}$ is halogen and the other is $C_{1-6}$ alkyl optionally substituted by one or more halogen, OH or $C_{1-6}$ alkoxy, or a group of formula III in which $R^8$ is H and one of $R^9$ and $R^{10}$ is H and the other is CN or $C_{1-6}$ alkyl optionally substituted by one or more halogen, OH or $C_{1-6}$ alkoxy, or a group of formula III in which $R^8$ is H and $R^9$ and $R^{10}$ are $C_{1-6}$ alkyl optionally substituted by one or more halogen, OH or $C_{1-6}$ alkoxy, or a group of formula III in which $R^8$ is $C_{1-6}$ alkyl optionally substituted by one or more halogen, OH or $C_{1-6}$ alkoxy and $R^9$ and $R^{10}$ are both H, or a group of formula IV.

More preferably $R^2$ is a group of formula II in which $R^7$ is $Si(CH_3)_3$, H, $CH_3$, $CH(CH_3)_2$, $CH_2OH$, $(CH_2)_2OH$, $CO_2CH_3$, Ph, thien-2-yl $CH_2OCH_3$, Br, Cl, or $CF_3$, or a group of formula III in which $R^8$, $R^9$ and $R^{10}$ are each H, or a group of formula III in which $R^8$, $R^9$ and $R^{10}$ are each Cl or a group of formula III in which $R^8$ and $R^9$ are Br and $R^{10}$ is H, or a group of formula III in which $R^8$ and $R^{10}$ are Br and $R^9$ is H, or a group of formula III in which $R^8$ and $R^9$ are Br and $R^{10}$ is $CH_3$, or a group of formula III in which $R^8$ and $R^{10}$ are Br and $R^9$ is $CH_3$, or a group of formula III in which $R^8$ and $R^{10}$ are Br and $R^9$ is Ph, or a group of formula III in which $R^8$ and $R^9$ are Br and $R^{10}$ is Ph, or a group of formula III in which $R^8$ and $R^{10}$ are Cl and $R^9$ is Ph, or a group of formula III in which $R^8$ and $R^9$ are Cl and $R^{10}$ is Ph, or a group of formula III in which $R^8$ and $R^{10}$ are Cl and $R^9$ is Br, or a group of formula III in which $R^8$ and $R^9$ are Cl and $R^{10}$ is Br, or a group of formula III in which $R^8$ is H and $R^{10}$ and $R^9$ are Br, or a group of formula III in which $R^8$ is H and $R^{10}$ and $R^9$ are Cl, or a group of formula III in which $R^8$ is H and $R^{10}$ and $R^9$ are F, or a group of formula III in which $R^8$ is H and $R^{10}$ is $CF_3$ and $R^9$ is Cl, or a group of formula III in which $R^8$ is H and $R^9$ is $CF_3$ and $R^{10}$ is Cl, or a group of formula III in which $R^8$ is H and $R^{10}$ is $CF_3$ and $R^9$ is Br, or a group of formula III in which $R^8$ is H and $R^9$ is $CF_3$ and $R^{10}$ is Br, or a group of formula III in which $R^8$ is H and $R^{10}$ is $CF_3$ and $R^9$ is F, or a group of formula III in which $R^8$ is H and $R^9$ is $CF_3$ and $R^{10}$ is F, or a group of formula III in which $R^8$ and $R^{10}$ are H and $R^9$ is CN, or a group of formula III in which $R^8$ and $R^9$ are Br and $R^{10}$ is $CF_3$, or a group of formula III in which $R^8$ and $R^{10}$ are Br and $R^9$ is $CF_3$, or a group of formula III in which $R^8$ is Br, $R^9$ is Br and $R^9$ is Cl, or a group of formula III in which $R^8$ is Br, $R^{10}$ is Br and $R^9$ is Cl, or a group of formula III in which $R^8$ is $CH_3$, $R^9$ and $R^{10}$ are Br, or a group of formula III in which $R^8$ is $CH_3$, $R^9$ and $R^{10}$ are F, or a group of formula II in which $R^8$ is $CH_3$, $R^9$ and $R^{10}$ are H, or a group of formula III in which $R^8$ is H, $R^9$ and $R^{10}$ are $CH_3$, or a group of formula III in which $R^8$, $R^9$ and $R^{10}$ are each Br, or a group of formula IV.

$R^3$ is preferably H, $C_{1-6}$ alkyL $NH_2$, $NH(C_{1-6}$ alkanoyl), $NH(C_{1-6}$ alkoxycarbonyl), $N(C_{1-6}$ alkoxycarbonyl)$_2$, $N(C_{1-6}$ alkyl)$_2$, N-pyrrolyl halogen or $S(O)_n(C_{1-6}$ alkyl optionally substituted by one or more halogen) where n is 0, 1 or 2.

$R^3$ is more preferably H, $CH_3$, $NH_2$, N-pyrrolyl, $N(CH_3)_2$, $NH(CO_2(t\text{-butyl}))$, $N(CO_2(t\text{-butyl}))_2$, $NHCOCH_3$, Br, Cl $SCH_3$ or $SCF_3$.

$R^4$ and $R^6$ are preferably halogen.

$R^4$ and $R^6$ are more preferably Cl.

$R^5$ is preferably $C_{1-6}$ alkyl optionally substituted by one or more halogen, $C_{1-6}$ alkoxy optionally substituted by one or more halogen, $C_{1-6}$ alkylthio optionally substituted by one or more halogen, $SF_5$ or halogen.

$R^5$ is more preferably $CF_3$, $OCF_3$, $SCF_3$ or $SF_5$.

The compounds (and salts thereof) which are most preferred are:

3-cyano-1-(2,6-dichloro-4-trifluoromethylphenyl)-4-ethynylpyrazole;
3-cyano-1-(2,6-dichloro-4-trifluoromethoxyphenyl)4-ethynylpyrazole;
3-cyano-1-(2,6-dichloro4-trifluoromethylsulphenylphenyl)4ethynylpyrazole;
4-(2-bromo-1,2-dichloroethenyl)-3-cyano-1-(2,6-dichloro-4-trifluoromethoxyphenyl)-pyrazole;
3-cyano-1-(2,6-dichloro-4-trifluoromethoxyphenyl)-4-tribromoethenylpyrazole;
4-(2,2-dibromoethenyl)-3-cyano-1-(2,6-dichlorowtrifluoromethylphenyl)- pyrazole;
3-cyano-4-(2,2-dichloroethenyl)-1-(2,6-dichloro-4-trifluoromethylphenyl)pyrazole;
3-cyano-1-(2,6-dichloro-4-trifluoromethylphenyl)4-(2,2-difluoroethenyl)pyrazole;
3-cyano-1-(2,6-dichloro-4-trifluoromethylphenyl)4- tribromoethenylpyrazole;
3-cyano-1-(2,6-dichloro-4-trifluoromethylphenyl)4-trichloroethenylpyrazole;
4-(2-bromo-1,2-dichloroethenyl)-3-cyano-1-(2,6-dichloro-4-trifluoromethylphenyl)-pyrazole;
4-(2-chloro-1,2-dibromoethenyl)-3-cyano-1-(2,6-dichloro-4-trifluoromethylphenyl)-pyrazole;
3-cyano-1-(2,6-dichloro-4-trifluoromethylphenyl)4-(1-methyl-2,2-dibromoethenyl)pyrazole;
3-cyano-1-(2,6-dichloro-4-trifluoromethylphenyl)4-(1-methyl-2,2-difluoroethenyl)pyrazole;
1-(2,6-dichloro-4-trifluoromethylphenyl)-4-ethynyl-3-trifluoromethylpyrazole;
4-(2-bromo-1,2-dichloroethenyl)-1-(2,6-dichloro-4-trifluoromethylphenyl)-3-trifluoromethylpyrazole; and
1-(2,6-dichloro-4-trifluoromethylphenyl)-4-ethynyl-3-methylpyrazole.

The compounds of the formula (I) may possess one or more asymmetric centres and so may exist in two or more stereoisomeric forms. The present invention includes all the individual stereoisomers of the compounds of formula (I) and mixtures thereof Separation of diastereoisomers may be achieved by conventional techniques, e.g. by fractional crystallisation, chromatography or H.P.L.C. of a stereoisomeric mnixture of a compound of formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystabisation of the diastereomeric salts formed by reaction of the corresponding racemate with a suitably optically active acid or base.

The invention further provides methods for the production of compounds of the invention, which are described below, and illustrated in the Examples.

Method 1

Preparation of a compound of formula I in which $R^2$ represents a group of formnula II (C≡$CR^7$), by reacting a compound of formula V,

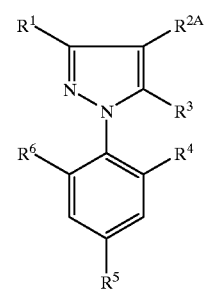

in which $R^1$ and $R^{3-6}$ are as defined above and $R^{2A}$ represents I, Br or trifluoromethylsulponate, with a compound of formula HC≡$CR^7$ where $R^7$ is as previously described. The reaction is preferably carried out in the presence of a palladium catalyst, for example bis(triphenylphosphine) palladium(II) chloride [$PdCl_2(PPh_3)_2$] and cuprous iodide. Alternatively the corresponding alkynylcuprate species generated from HC≡$CR^7$ may be preformed and reacted with the compound of formula V as defied above. The reaction is p referably carried out in a solvent which does not adversely affect the reaction (for example triethylamine and/or dimethylformamide (DMF)).

Compounds of formula I in which $R^2$ is $C\equiv CR^7$ may be interconverted using conventional methods: for example, compounds in which $R^7$ is $C_{1-6}$ trialkylsilyl may be converted to compounds in which $R^7$ is H by the action of a base such as potassium carbonate in a solvent such as methanol.

Compounds of formula V in which $R^{2A}$ represents I or Br may be prepared from a corresponding compound of formula V in which $R^{2A}$ represents H by reaction with an iodinating or brominating agent such as N-(iodo or bromo) succinimide.

Compounds of formula V in which $R^{2A}$ represents H are available commercially or are available by conventional methods or methods described herein and suitable adaptation thereof Method 2

Preparation of a compound of formula I in which $R^2$ represents a group of formula III by reaction of a compound of formula V where $R^{2A}$ is I with a suitable vinyl species such as a vinyl(trialkyl)tin species, optionally in the presence of a catalytic amount of a Pd species, and then where necessary halogenating the resulting compound. The reaction is preferably carried out in the presence of a palladium catalyst, for example tetrakis(triphenylphosphine)palladium (0) or palladium acetate. The reaction is preferably carried out in a solvent which does not adversely affect the reaction (for example triethylamine or DMF), at or around 75° C. The halogenation may be carried out using conventional techniques.

Method 3

Preparation of a compound of formula I in which $R^2$ represents a group of formula IV, by reacting a compound of formula V as defined above in which $R^{2A}$ represents H, with cyclohexanone. The reaction is preferably carried out in an organic acid (for example acetic acid), at or around 120° C.

Compounds of formula V in which $R^1$ represents CN, $NO_2$, CHO, $C_{1-6}$ alkanoyl or $C_{1-6}$ alkyl optionally substituted by one or more halogen atoms; $R^{2A}$ represents H; $R^3$ represents $NH_2$, OH, $C_{1-6}$ alkoxy or $S(O)_n(C_{1-6}$ alkyl optionally substituted by one or more halogen); and $R^{4-6}$ are as defined above are either known or available using known techniques.

Method 4

Preparation of a compound of formula I in which $R^1$ represents $C_{1-6}$ alkoxycarbonyl, by treating a corresponding compound of formula I in which $R^1$ represents CN with a base in the presence of the appropriate alcohol. Suitable bases include potassium carbonate and potassium hydroxide. The reaction may be carried out at or around room temperature.

Method 5

Preparation of a compound of formula I in which $R^3$ represents halogen, by treating a corresponding compound of formula I in which $R^3$ represents $NH_2$ with an alkyl nitrite such as n-butyl nitrite and a suitable halide source. Suitable halide sources include bromoform The reaction is preferably carried out in a solvent which does not adversely affect the reaction (for example acetonitrile), at or around 70° C.

Method 6

Preparation of a compound of formula I in which $R^3$ represents H, by treating a corresponding compound of formula I in which $R^3$ represents $NH_2$ with an alkyl nitrite such as t-butyl nitrite. The reaction is preferably carried out in a suitable solvent which does not adversely affect the reaction (for example tetrahydrofuran), at the reflux temperature of the solvent.

Method 7

Preparation of a compound of formula I in which $R^3$ represents N-pyrrolyl, by treating a corresponding compound of formula I in which $R^3$ represents $NH_2$ with a 2,5-dialkoxy tetrahydrofuran, such as 2,5-dimethoxytetrahydrofilran, in the presence of an acid. The reaction is preferably carried out using an organic acid such as acetic acid, at elevated temperature, such as the reflux temperature of acetic acid.

Method 8

Preparation of a compound of formula I in which $R^3$ represents $S(O)_n(C_{1-6}$ alkyl optionally substituted by one or more halogen), by treating a corresponding compound of formula I in which $R^3$ represents $NH_2$ with an alkyl nitrite such as n-butyl nitrite and a di($C_{1-6}$ alkyl optionally substituted by one or more halogen) disulphide, and if neccessary oxidising the compound of formula I in which $R^3$ represents $S(C_{1-6}$ alkyl optionally substituted by one or more halogen). A compound of formula I in which $R^3$ represents $S(O)_n(C_{1-6}$ alkyl optionally substituted by one or more halogen) and n is 1 or 2 can be made by oxidising a compound of formula I in which $R^3$ represents $S(O)_n(C_{1-6}$ alkyl optionally substituted by one or more halogen) and n is 0 or 1. The reaction is preferably carried out by heating the compound of formula I where $R^3$ is $NH_2$ with the disulphide compound in a suitable solvent which does not adversely affect the reaction (for example acetonitrile), at elevated temperatures, followed by addition of the allyl nitrite and further heating. The oxidation of the sulphide (or sulphoxide) can be carried out using conventional methods, for example by the use of pertrifluoroacetic acid.

Method 9

Preparation of a compound of formula I in which $R^2$ is a group of formula III in which each of $R^{9-10}$ is halogen by reacting a compound of formula V in which $R^1$ and $R^{3-6}$ are as defined above and $R^{2A}$ is $COR^8$ with a tri(alkyl or aryl)-substituted phosphine and a carbon tetrahalide. The trisubstitiuted phosphine is preferably triphenyiphosphine.

Compounds of formula V in which $R^{2A}$ represents $CO(C_{1-6}$ alkyl optionally substituted by one or more halogen) may be prepared from a corresponding compound of formula I where $R^2$ represents $C(C_{1-6}$ alkyl optionally substituted by one or more halogen)$=CH_2$ by reaction with an oxidising system such as N-methylmorpholine oxide/osmium tetronide (cat.)/sodium metaperiodate. Alternatively, compounds of formula V in which $R^{2A}$ represents $CO(CH_2(C_{1-5}$ alkyl optionally substituted by one or more halogen)) may be prepared from a corresponding compound of formula I where $R^2$ represents a group of formula II where $R^7$ is ($C_{1-5}$ alkyl optionally substituted by one or more halogen) by hydration, for example by reaction with toluenesulphonic acid hemihydrate in wet acetonitrile.

Method 10

Preparation of a compound of formula I in which $R^2$ is a group of formula III in which $R^8$ is H and one of $R^9$ and $R^{10}$ is halogen and the other is $CF_3$ by reaction of a compound of formula V in which $R^1$ and $R^{3-6}$ are as defined above and $R^{2A}$ is CHO with a compound of formula (halogen)$_3$CCF$_3$ in the presence of a zinc halide such as zinc chloride, and a cuprous halide such as cuprous chloride. The reaction is preferably carried out in the presence of a polar solvent such as N,N-dimethylformamide.

Preparation of a compound of formula I in which $R^2$ is a group of formula III in which $R^8$ is H and one of $R^9$ and $R^{10}$ is Cl, Br or I and the other is C(Cl, Br or I)$_3$ are available in an analogous manner using reagents of the formula (Cl, Br or I)$_3$CC(Cl Br or I)$_3$. The less reactive C-halogen bond is not broken and the C(Cl, Br or I)$_3$ moiety containing this bond is transferred in an analogous manner to the trnsfer of the CF$_3$ moiety above.

Compounds of formula V in which $R^{2A}$ represents CHO may be prepared from a corresponding compound of formula I where $R^2$ represents ethenyl by reaction with an oxidising system such as N-methylmorpholine oxide/osmium tetroxide (cat.)/sodium metaperiodate.

Method 11

Preparation of a compound of formula I in which $R^2$ is a group of formula II in which by reaction of a compound of formula V above where $R^{2A}$ is I with a $R^7$—C≡C—Sn species such as a $R^7$—C≡C—Sn(alkyl)$_3$ compound. The reaction is preferably carried out in the presence of a palladium catalyst, for example tetrakis(triphenylphosphine)palladium(0). The reaction is preferably carried out in a solvent which does not adversely affect the reaction (for example dimethylformamide), at or around 75° C.

Method 12

Preparation of a compound of formula I in which $R^2$ is a group of formula II and $R^7$ is not H by reaction of a compound of formula I in which $R^2$ is a group of formula II and $R^7$ is H with a reagent capable of reacting as a $R^7)^+$ synthon, such as $R^7Z$, where Z is a suitable leaving group such as chloro, bromo, iodo, or an alkyl or arylsulphonate, optionally in the presence of a base. The reaction can be carried out with a $R^7$I species for instance in the presence of cuprous iodide a Pd$^{II}$ species such as bis(triphenylphosphine)palladium (II) chloride and a base such as triethylamrine.

Method 13

Preparation of a compound of formula I in which $R^2$ is a group of formula II and $R^7$ is $C_{1-6}$ alkoxycarbonyl by reaction of a compound of formula I in which $R^2$ is a group of formula II and $R^7$ is CN with a $C_{1-6}$ alcohol, optionally in the presence of a base. Suitable bases include potassium carbonate and potassium hydroxide. The reaction may be carried out at or around room temperature.

Method 14

Preparation of a compound of formula I in which $R^2$ is a group of formula II and $R^7$ is $C_{1-6}$ alkoxycarbonyl by oxidation of a compound of formula I in which $R^2$ is a group of formula II and $R^7$ is CH$_2$OH to give the corresponding acid, followed by esterification with a $C_{1-6}$ alcohol. The process is conveniently carried out using manganese dioxide/potassium cyanide in the alcohol.

Method 15

Preparation of a compound of formula I in which $R^3$ is NH($C_{1-6}$ alkanoyl) by reaction of a compound of formula I in which $R^3$ is NH$_2$ with an acylating agent such as a $C_{1-6}$ alkanoyl(chloride, bromide or iodide). The process is preferably carried out with the acid chloride and an acid acceptor such as pyridine.

Method 16

Preparation of a compound of formula I in which $R^3$ is N($C_{1-6}$ alkoxycarbonyl)$_2$ by reaction of a compound of formula I in which $R^3$ is NH$_2$ with a di($C_{1-6}$ allyl) dicarbonate. The process is preferably carried out using a base system such as triethylamine/4dimethylaminopyndine (DMAP) in a solvent such as DMF.

Method 17

Preparation of a compound of formula I in which $R^3$ is NH($C_{1-6}$ alkoxycarbonyl) by reaction of a compound of formula I in which $R^3$ is N($C_{1-6}$ alkoxycarbonyl)$_2$ with an acid. The process is preferably carried out using trifluoroacetic acid (TFA) in a solvent such as dichloromethane.

Method 18

Preparation of a compound of formula I in which $R^3$ is N($C_{1-6}$ alkyl)$_2$ by reaction of a compound of formula I in which $R^3$ is NH$_2$ with a $C_{1-6}$ alkylating agent such as an alkyl(chloride bromide or iodide). Preferably the reaction is carried out using the alkyl iodide. Preferably the reaction is carried out in the presence of a base such as NaH. Preferably the reaction is carried out in a suitable sovent such as THF.

Compounds of formula I in which $R^3$ is an amio derivative may be prepared from compounds of formula I in which $R^3$ is NH$_2$ using conventional methods, such as those described above.

Method 19

Preparation of a compound of formula I in which $R^2$ represents a group of formula III where some or all of $R^8$, $R^9$ and $R^{10}$ are halogen by reaction of a compound of formula I in which $R^2$ represents a group of formula II with a halogen, optionally in the presence of a base. An example is the reaction of the alkyne where $R^7$ is H with butyllithium followed by the halogen source, suitably in an ether solvent, to give compounds where $R^8$, $R^9$ and $R^{10}$ are all halogen. Reaction of the alkyne with any $R^7$ group with the halogen source (such as Cl$_2$Br$_2$ or I$_2$) gives 1,2-dihalo compounds.

Method 20

Preparation of a compound of formula I in which $R^2$ represents a group of formula II by reaction of a compound of formula V where $R^{2A}$ is I with a compound of formula HC≡C—$R^7$ in the presence of butyllithium, zinc chloride and a Pd species. The reaction is preferably carried out in the presence of a suitable base such as triethylamine and in a suitable solvent such as DMF. Preferably the alkyne is dissolved in a suitable solvent such as THF, treated with butyllithium at reduced temperature, zinc chloride in solvent is then added and the temperature allowed to rise to ambient. Preferably the mixture is cooled again and the palladium species, such as bis(triphenylphosphine)palladium chloride, is added together with the compound of formula V where $R^{2A}$ is I. Preferably the reaction temperature is then raised, for example to the reflux temperature of the solvent.

Method 21

Preparation of a compound of formula I in which $R^2$ represents a group of formula II where $R^7$ is a halogen by reaction of a compound of formula I in which $R^2$ represents a group of formula III where $R^8$ is H and $R^9$ and $R^{10}$ are halogen with a base such as 1,8-diazabicyclo[5.4.0]undec-7-ene (DBU).

Method 22

Preparation of a compound of formula I in which $R^2$ represents a group of formula III where $R^8$ is H, phenyl or alkyl by reaction of a compound of formula V where $R^2$ is $COR^8$ with a $R^9R^{10}C=Ti$ species. An example of a $R^9R^{10}C=Ti$ species is $\mu$-chloro-$\mu$-methylene-[bis(cyclopentadienyl)titanium]dimethylaluminium (the "Tebbe reagent"). Preferably the compound of formula V where $R^{2A}$ is $COR^8$ is dissolved in an inert solvent such as tetrahydrofuran (THF), cooled under an inert atmosphere, then the titanium carbene species is added, and the mixture is allowed to warm up.

Method 23

Preparation of a compound of formula I in which $R^2$ represents a group of formula III where $R^8$ is H by reaction of a compound of formula V where $R^{2A}$ is CHO with a $R^9R^{10}$ CH-phosphonium species (Wittig reaction), a $R^9R^{10}$ CH-silyl species Peterson olefination), or a $R^9R^{10}$CH-phosphonate species (Homer-Emmons reacion or Wadsworth-Emmons reaction), in the presence of a base. Such reagents are available commercially or via conventional means.

Method 24

Preparation of a compound of formula I where $R^2$ is a group of formula III by reaction of a compound of formula V where $R^{2A}$ is H with a compound of formula $R^8COCHR^9R^{10}$. The reaction is preferably carried out in an organic acid (for example acetic acid), preferably at elevated temperatures such as around 120° C.

Method 25

Where desired or necessary converting a compound of the formula I into a pharmaceutically or veterinarily acceptable salt thereof A pharmaceutically or veterinarily acceptable salt of a compound of formula (I) may be readily prepared by mixing together solutions of a compound of the formula (I) and the desired acid or base, as appropriate. The salt may be precipitated from solution and be collected by filtration or may be recovered by other means such as by evaporation of the solvent.

Compounds of the invention are available by either the methods described herein in the Methods and Examples or by conventional methods known to those skilled in the art, or suitable adaptation thereof using methods known in the art.

The compounds of the invention may be separated and purified by conventional methods. It will be apparent to those skilled in the art that sensitive functional groups may need to be protected and deprotected during synthesis of a compound of the invention. This may be achieved by conventional techniques, for example as described in the publication 'Protective Groups in Organic Synthesis' by T W Greene and P G M Wuts, John Wiley and Sons Inc, 1991.

The compounds of the invention are useful because they possess parasiticidal activity in humans, animals and plants. They are particularly useful in the treatment of ectoparasites.

Dealing first with use of the compounds of the invention in humans, there is provided:

a) a pharmaceutical formulation comprising a compound of the invention in admixture with a pharmaceutically acceptable adjuvant, diluent or carrier which may be adapted for topical administration;

b) a compound of the invention, for use as a medicament;

c) the use of a compound of the invention in the manufacture of a parasiticidal medicament; and d) a method of treating a parasitic infestation in a patient which comprises administering an effective amount of a compound of the invention to the patient.

Turning now to the use of the compounds of the invention in animals, the compounds may be administered alone or in a formulation appropriate to the specific use envisaged and to the particular species of host animal being treated and the parasite involved. Methods by which the compounds may be administered include, orally in the form of a capsule, bolus, tablet or drench or as a pour-on or spot-on formulation, or alternatively, they can be administered by injection (e.g. subcutaneously, intramuscularly or intravenously) or as an implant or as a dip or spray or via a dust-bag or shampoo.

Such formulations are prepared in a conventional manner in accordance with standard pharmaceutical and veterinary practice. Thus capsules, boluses or tablets may be prepared by mixing the active ingredient with a suitable finely divided diluent or carrier additionally containing a disintegrating agent and/or binder such as starch, lactose, talc or magnesium stearate. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The liquid formulations are prepared by dissolving or suspending the active ingredient in the liquid carrier such that the final formulation contains from 0.5 to 60% by weight of the active ingredient. Solid formulations are prepared by methods well known in the art.

These formulations will vary with regard to the weight of active compound depending on the species of host animal to be treated, the severity and type of infection and the body weight of the host. For parenteral, topical and oral administration, typical dose ranges of the active ingredient are 0.1–50 mg per kg of body weight of the animal, preferably in the range 1–5 mg per kg.

As an alternative the compounds may be administered with the animal feedstuff and for this purpose a concentrated feed additive or premix may be prepared for mixing with the normal animal feed.

The compounds of the invention have utility in the control of arthropod, plant nematode, helminth or protozoan pests. The compounds of the invention may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fish, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculus*, Haemaphysalis spp., Dermacentor spp., Ornithodorus spp. (e.g. *Ornithodorus moubata* and mites (e.g.

Damalinia spp., *Dermahyssus gallinae,* Sarcoptes spp. e.g. *Sarcoptes scabiei,* Psoroptes spp., Chorioptes spp., Demodex spp., Eutrombicula spp.,) Diptera (e.g. Aedes spp., Anopheles spp., Musca spp., Hypoderma spp., Gastrophilus spp., Simulium spp.); Hemiptera (e.g. Triatoma spp.); Phthiraptera (e.g. Damalinia spp., Linoqnathus spp.) Siphonaptera (e.g. Ctenocephalides spp.); Dictyoptera (e.g. Periplaneta spp., Blatella spp.); Hymenoptera (e.g. *Monomorium pharaonis*); for example against infections of the gastrointestinal tract caused by parasitic nematode worms, for example members of the family Trichostrongylidae, *Nippostronylus brasiliensis, Trichinella spiralis, Haemonchus contortus, Trichostronylus colubrnformis, Nematodirus battus, Ostertagia circumcincta, Trichostrongylus axei,* Cooperia spp. and *Hymenolepis nana,* in the control and treatment of protozoal diseases caused by, for example Eimeria spp. e.g. *Eimeria tenella, Eimeria acervulina, Eimeria brunetti, Elmeria maxima, Eimeria necatrix, Eimeria bovis, Eimeria zuerni and Eimeria ovinoidalis; Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal foodstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in water-ways, wells, reservoirs or other running or standing water; for the treatment of foundations, structure and soil in the prevention of the attack on buildings by termites, for example, Reticulitermes spp., Heterotermes spp., Coptoterms spp.; in agriculture, against adults, larvae and eggs of Lepidoptera (butterflies and moths), e.g. Heliothis spp. such as *Heliothis virescens* (tobacco budworm), *Heliothis annioera* and *Heliothis zea,* Spodoptera spp. such as *S. exempta, S. littoralis* (Egyptian cotton worm), *S. eridania* (southern army worm), *Mamestra configurata* (bertha army worm); Earias spp. e.g. *E. insulana* (Egyptian bollworm), Pectinophora spp. e.g. *Pectinophora gossyiella* (pink bollworm), Ostrinia spp. such as *O. nubilalis* (European cornborer), *Trichoplusia ni* (cabbage looper), Pieris spp. (cabbage worms), Laphyqma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond black moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Melioethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp.; Nymenoptera e.g. Athalia spp. and Cephus spp. (saw flies), Atta spp. (leaf cutting ants); Diptera e.g. Hylemyia spp. (root flies), Atherigona spp. and Chlorops spp. (shoot ffies), Phytomyza spp. (leaf miners), Ceratitis spp. (fruit flies); Thysanoptera such as *Thrips tabaci:* Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphacotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meliodogyne spp. (e.g. *M. incognita*); cyst nematodes such as Globodera spp. (e.g. *G. rostochiensis*); Heterodera spp. (e.g. *H. avenae*); Radopholus spp. (e.g. *R similis*); lesion nematodes such as Pratylenchus spp. (e.g. *P. pratensis*); Belonoliamus spp. (e.g. *B. gracilis*); Tylenchulus spp. (e.g. *T. semipenetrans*); Rotylenchulus spp. (e.g. *R reniformis*); Rotylenchus spp. (e.g. *R robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T primitivus*); dagger nematodes such as Xiphinema spp. (e.g. *X diversicaudatum*), Longidorus spp. (e.g. *L. elongatus*); Hoplolaimus spp. (e.g. *H. coronatus*); Aphelenchoides spp. (e.g. *A. ritzemabosi, A. besseyi*); stem and bulb eelworms such as Ditylenchus spp. (e.g. *D. dipsaci*).

The compounds of the invention also have utility in the control of arthropod or nematode pests of plants. The active compound is generally applied to the locus in which arthropod or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 1 g to 1000 g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of the invention may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of the invention are of value in controlling pests which feed on parts of the plant remote from the point of application, e.g. leaf feeding insects are killed by the subject compounds applied to roots. In addition the compounds may reduce attacks on the plant by means of antifeeding or repellent effects.

The compounds of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobfids), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of the invention are of value in the control or arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have their market value substantially reduced as a result of the infection.

Administration of a small amount of a compound of the invention preferably by combination with poultry feed is effective in preventing or greatly reducing the incidence of coccidiosis. The compounds are effective against both the cecal form (caused by *E. tenella*) and the intestinal forms (principally caused by *E. acervulina, E. brunetti, E. maxima* and *E. necatrix*).

The compounds of the invention also exert an inhibitory effect on the oocysts by greatly reducing the number and or the sporulation of those produced.

Therefore, according to a further aspect of the invention, there is provided a veterinary parasiticidal formulation comprising a compound of the invention, in admixture with a compatible adjuvant, diluent or carrier. Preferably, the fomudlation is adapted for topical admi ation The invention further provides a compound of the invention for use as a parasiticide; and a method of treating a parasitic infesttion at a locus, which comprises treatment of the locus with an effective amount of a compound of the invention. Preferably, the locus is the skin or fuir of an animal or a plant or seed or the area surrounding the plant or seed.

The invention further provides a method of harming or killing a parasite which comprises administering to said parasite or the locus thereof an effective amount of a compound of the formula (I), or salt or formulation thereof as previously described.

It is to be appreciated that reference to treatment includes prophylaxis as well as the alleviation of established symptoms of a parasitic infestation.

Test for Insecticidal Activity

Adult flies (Stomoxys calcitrans) are collected and anaesthetized using $CO_2$. 1 µl of an acetone solution containing the test compound is applied directly to the thorax of the fly. Flies are then placed careffilly into a 50 ml tube covered with damp gauze to recover from the $CO_2$. Negative controls have 1 µl of acetone dispensed onto them. Mortality is assessed 24 hours after dosing.

The invention is illustrated by the following examples in which: melting points were determined using a Gallenkamp melting point apparatus and are uncorrected; nuclear magnetic resonance data were obtained using a Bruker AC300 or AM300; mass spectral data were obtained on a Finnigan Mat. TSQ 7000 or a Fisons Instruments Trio 1000—the calculated and observed ions quoted refer to the isotopic composition of lowest mass.

EXAMPLES

Example A1 (llustrative)
5-Amino-3-cyano-1-(2,6-dichloro-4-trifluoromethylphenl)-4-iodopyrazole To a stirred solution of 5-amino-3-cyano-1-(2,6-dichloro-4-trifluoromethylphenyl)pyrazole (5.0 g, the compound of Reference Example 1 from EP 295,117 A1), in acetonitrile (60 ml) at room temperature was added N-iodosuccinimide (3.52 g), portionwise over a period of five minutes. Stirring was continued for lhr and the mixture was then evaporated to dryness to provide the crude product (8.2 g), still containing succinimide. This may be used without further purification or, if desired, purified by partitioning between dichloromethane and water, separating, drying ($MgSO_4$) and evaporating the organic layer to produce a yellow solid. Trituration with hexane provides the title compound as a white solid, m.p. 213° C. (decomp.).

Example A2
5-Amino-3-cyano-1-(2,6-dichloro-4-trifluoromethylphenyl)-4-trimethylsilylethynlpyrazole To a stirred solution of 5-amino-3-cyano-1-(2,6-dichloro-4-trifluoromethylphenyl)4-iodopyrazole (6.96 g, crude from Example A1) in triethylamine (30 ml) and dimethylformamide (6 ml) at room temperature was added trimethylsilylacetylene (3 ml), cuprous iodide (150 mg) and bis (triphenylphosphine)palladium (II) chloride (300 mg). The mixture was heated at 50–60° C. for one hour, trimethylsilylacetylene (0.3 ml) was then added and stirring and heating continued for a further period of 30 minutes. The cooled reaction mixture was diluted with water (250 ml) and extracted with ether (250 ml). The organic layer was separated (aided by the addition of brine). The aqueous layer was re-extracted with ether (250 ml). The combined ether extracts were dried ($MgSO_4$) and evaporated to give the crude product as a gum (4.67 g). Purification by column chromatography on silica gel eluted with dichloromethane-:hexane (1:1) followed by recrystallisation from ether/hexane provided the title compound as a white solid m.p. 181–2° C.

$^1$H NMR ($CDCl_3$) δ: 0.2 (s, 9H), 4.1 (br. s, 2H), 7.7 (s, 2H)

MS (thennospray): M/Z[$M+NH_4$]434.2; $C_{16}H_{13}Cl_2F_3N_4Si+NH_4$ requires 434.0

Example A3
5-Amino-3-cyano-1-(2.6-dichloro-4-triuoromethylphenyl14-ethynylpyrazole To a stirred solution of 5-amino-3-cyano-1-(2,6-dichloro-4-trifluoromethylphenyl)4-trimethylsilylethynylpyrazole (2.0 g, crude from Example A2) in methanol (30 ml) was added potassium carbonate (1 g). After 10 minutes at room temperature the reaction mixture was partitioned between ether (100 ml) and water (100 ml). The organic layer was separated, washed with brine (100 ml), dried ($MgSO_4$) and evaporated. The residue was purified by column chromatography on silica gel eluted with dichloromethane followed by recrystallisation from ether to provide the title compound as a white solid m.p. 215–216° C.

$^1$H NMR ($CDCl_3$) δ: 3.49 (s, 1H), 4.2 (br. s, 2H), 7.8 (s, 2H)

MS (thermospray): M/Z[$M+NH_4$]362.4; $C_{13}H_5Cl_2F_3N_4+NH_4$ requires 362.0

Example A4
5-Amino-3-cyano-1-(2.6-dichloro-4-trifluoromethylphenyl)4-(prop-1-ynyl)pyrazole To a stirred solution of 5-amino-3-cyano-1-(2,6-dichloro-4-trifluoromethylphenyl)4-iodopyrazole (0.904 g, the compound of Example A1) in dimethylformamide(2 ml) and triethylamine (10 ml) contained in a stainless steel bomb was added cuprous iodide (60 mg) and bis (triphenylphosphine)palladium(II) chloride (120 mg). The reaction vessel was cooled to −78° C. and propyne (2 g) condensed into it. The vessel was sealed and then heated at 70° C. for 18 hours and then left at room temperature for 2 days. The reaction mixture was partitioned between ether and water. The organic layer was separated, washed with brine, dried ($MgSO_4$) and evaporated. The residue was purified by column chromatography on silica gel eluted with dichloromethane : hexane (1:1) to provide the title compound as a white solid m.p. 226–8° C.

$^1$H NMR ($CDCl_3$) δ: 2,2 (s, 3H), 4.19 (br. s, 2H), 7.78 (s, 2H)

MS (thermospray): M/Z[M+H]358.9; $C_{14}H_7Cl_2F_3N_4+H$ requires 359.0

Example A5
5-Amino-3-cyano-1-(2,6-dichloro-4-trifluoromethylphenyl)-4-(3-methylbut-1-ynyl)pyrazole To a stirred solution of 5-amino-3-cyano-1-(2,6-dichloro-4-trifluoromethylphenyl)-4-iodopyrazole (447 mg, the compound of Example A1) in triethylamine (10 ml) at room temperature was added 3-methylbut-1-yne (0.5 ml), cuprous iodide (15 mg) and bis(triphenylphosphine)palladium(II) chloride (30 mg). The reaction mixture was heated at 70° C. for two hours. The reaction mixture was partitioned between ether (100 ml) and water (100 ml). The organic layer was separated, washed with brine, dried ($MgSO_4$) and evaporated. The residue was purified by column chromatography on silica gel eluted with dichloromethane: hexane (1:1) to provide the title compound as a pale yellow solid m.p. 210–2° C.

$^1$H NMR ($CDCl_3$) δ: 1.3 (d, 6H), 2.83 (h, 1H), 4.0 (br. s, 2H), 7.78 (s, 2H).

MS (thermospray): M/Z[M+H]387.0; $C_{16}H_{11}Cl_2F_3N_4+H$ requires 387.0

Example A6
5-Amino-3-cyano-1-(2,6-dichloro-4-trifluoromethylphenyl)-4-(3-hydroxyprop-1-ynyl)pyrazole To a stirred solution of 5-amino-3-cyano-1-(2,6-dichloro-4-trifluoromethylphenyl)-4-iodopyrazole (200 mg, the compound of Example A1) in triethylamine (2 ml) and dimethylformamide (1 ml) at room temperature was added propargyl alcohol (0.2 ml), cuprous iodide (10 mg) and bis(triphenylphosphine)palladium(II) chloride (20 mg). The reaction mixture was heated at 70° C. for two hours. The reaction mixture was partitioned between ether (10 ml) and water (10 ml). The organic layer was separated, washed with brine, dried ($MgSO_4$) and evaporated. The residue was purified by column chromatography on silica gel eluted with ether:dichloromethane (10:1) to provide the title compound as a pale yellow solid m.p. 237–9° C.

$^1$H NMR ($d_6$-DMSO) δ: 4.32 (d, 2H), 5.3 (t, 1H), 6.58 (br. s, 1H), 8.28 (s, 2H)

MS (thermospray): M/Z[$M+NH_4$]391.8; $C_{14}H_7Cl_2F_3N_4O+NH_4$ requires 392.0

Example A7
5-Amino-3-cyano-1-(2,6-dichloro-4-trifluoromethylphenyl?-4-(4-hydroxybut-1-ynyl)pyrazole To a stirred solution of 5-amino-3-cyano-1-(2,6-dichloro-4-trifluoromethylphenyl)4-iodopyrazole (447 mg, the compound of Example A1) in triethylamine (20 ml) and dimethylformamide (2 ml) at room temperature was added 3-butyne-1-ol (0.5 ml), cuprous iodide (15 mg) and bis (triphenylphosphine)paliadium(II) chloride (30 mg). The reaction mixture was heated at 70° C. for two hours. The reaction mixture was partitioned between ether (10 ml) and water (10 ml). The organic layer was separated, washed with brine, dried ($MgSO_4$) and evaporated. The residue was purified by column chromatography on silica gel eluted with ether to provide the title compound as a light brown solid m.p. 215–6° C.

$^1$H NMR ($CDCl_3$) δ: 2.72 (t, 2H), 3.49 (m, 1H), 3.87 (m, 2H), 4.1 (br. s, 1H), 7.8 (s, 2H)

MS (thermospray): M/Z[$M+NH_4$]406.4; $C_{15}H_9Cl_2F_3N_4O+NH_4$ requires 406.0

Example A8
5-Amino-3-cyano-1-(2,6-dichloro-4-trifluoromethylphenyl)-4-methoxycarbonylethynylpyrazole To a stirred solution of 5-amino-3-cyano-1-(2,6-dichloro-4-trifluoromethylphenyl)4-(3-hydroxyprop-1-ynyl)pyrazole (250 mg, the compound of Example A6) in ether (10 ml) was added manganese dioxide (1 g) and the mixture stirred at room temperature for two hours. Methanol (2 ml) and potassium cyanide (250 mg) were then added and stirring continued for 15 minutes. The reaction mixture was filtered and evaporated to dryness. The residue was purified by chromatography on silica gel eluted with dichloromethane.

Combination and evaporation of appropriate fractions provided the title compound as a light brown solid m.p. 201–2° C.

$^1$H NMR (CDCl$_3$) δ: 3.82 (s, 3H), 4.6 (br. s, 2H), 7.81 (s, 2H)

MS (thermospray): M/Z[M+NH$_4$]420.5; C$_{15}$H$_7$Cl$_2$F$_3$N$_4$O$_2$+NH$_4$ requires 420.0

Example A9

5-Amino-3-cyano-1-(2,6-dichloro-4-trifluoromethlphenyl)-4-phenylethynyl) pyrazole To a stirred solution of 5-amino-3-cyano-1-(2,6-dichloro-4-trifluoromethylphenyl)-4-iodopyrazole (250 mg, the compound of Example A1) in dimethylformamide (2 ml) at room temperature was added 2-phenylethynyltri-n-butyltin (0.6 ml) and tetrakis(triphenylphosphine)palladium(0) (30 mg). The reaction mixture was heated at 75° C. for two hours and then left overnight at room temperature. The reaction mixture was partitioned between ether and water. The organic layer was separated, washed with brine, dried (MgSO$_4$) and evaporated. The residue was purified by column chromatography on silica gel eluted initially with hexane: dichloromethane (1:1) and then dichloromethane to provide the title compound as a pale yellow amorphous solid m.p. 265–267° C.

$^1$H NMR (CDCl$_3$) δ: 4.21 (br. s, 2H), 7.38 (m, 3H), 7.54 (m, 2H), 7.8 (s, 2H)

MS (thermospray): M/Z[M+H]420.8 ; Cl$_{19}$H$_9$Cl$_2$F$_3$N$_4$+H requires 421.0

Example A10

5-Amino-3-cyano-1-(2,6-dichloro-4-trifluoromethylphenyl-4-thien-2-ylethynyl)pyrazole To a stirred solution of 5-amino-3-cyano-1-(2,6-dichloro-4trifluoromethylphenyl)-4-ethynylpyrazole (200 mg, the compound of Example A3) in triethylamine (4 ml) and dimethylformamide (1 ml) at room temperature was added 2-iodothiophene (0.5 ml), cuprous iodide (15 mg) and bis(triphenylphosphine)palladium(H) chloride (30 mg). The reaction mixture was heated at 60° C. for one hour. The reaction mixture was partitioned between ether (100 ml) and water (100 ml). The organic layer was separated, washed with brine, dried (MgSO$_4$) and evaporated. The residue was purified by column chromatography on 15 silica gel eluted with hexane: dichloromethane (1:1) to provide the title compound as a light brown solid m.p. 262° C. decomp.

$^1$H NMR (CDCl$_3$) δ: 4.23 (br. s, 2H), 7.05 (m, 1H), 7.45 (m, 2H), 7.8 (s, 2H)

MS (thermospray): M/Z[M+H]426.6; C$_{17}$H$_7$Cl$_2$F$_3$N$_4$S+H requires 427.0

Example A11

5-Amino-3-cyano-1-(2,6-dichloro-4-trifluoromethylphenyl) 4-(methoxyprop-1-ynyl)pyrazole To a stirred solution of 5-amino-3-cyano-1-(2,6-dichloro-4-trifluoromethylphenyl)4-iodopyrazole (200 mg, the compound of Example A1) in triethylamine (2 ml) and dimethylformamide (1 ml) at room temperature was added methyl propargyl ether (0.5 ml), cuprous iodide (15 mg) and bis(triphenylphosphine)palladium(II) chloride (30 mg). The reaction mixture was heated at 70° C. for two hours. The reaction mixture was partitioned between ether (50 ml) and aqueous citric acid solution (50 ml, 20%). The organic layer was separated, washed with water, dried (MgSO$_4$) and evaporated. The residue was purified by column chromatography on silica gel eluted with dichloromethane to provide the title compound as a pale yellow solid m.p. 210° C. decomp.

$^1$H NMR (CDCl$_3$) δ: 3.48 (s, 3H), 4.2 (br. s, 2H), 4.89 (s, 2H), 7.8 (s, 2H)

MS (thermospray): M/Z[M+NH4]406.0; C$_{15}$H$_9$Cl$_2$F$_3$N$_4$O+NH$_4$ requires 406.0

Example A12

5-Amino-1-(2,6-dichloro-4-triuoromethylphenyl)-3-ethoxycarbonyl-4-ethynylpyrazole To a stirred solution of potassium hydroxide (0.25 g) in ethanol (3 ml) was added 5-amino-3-cyano-1-(2,6-dichloro-4-trifluoromethylphenyl)4-trimethylsilylethynylpyrazole (0.21 g). After 30 minutes at 30° C. the reaction mixture was poured onto a mixture of water (10 ml) and ice (10 g). Ether (30 ml) was added. The organic layer was separated. The aqueous layer was extracted with ether (30 ml, x2). The combined organic layers were dried (MgSO$_4$) and evaporated. The residue was purified by column chromatography on silica gel (4 g) eluting with dichloromethane. Combination and evaporation of suitable fractions followed by recrystallisation from ether/hexane provided the title compound as a pale orange solid, m.p. 152–154° C.

$^1$H NMR (CDCl$_3$) δ: 1.42 (t, 3H), 3.49 (s, 1H), 4.11 (br. s, 2H), 4.43 (q, 2H), 7.78 (s, 2H)

MS (thermospray): M/Z[M]391.3; C$_{15}$H$_{10}$Cl$_2$F$_3$N$_3$O$_2$ requires 391.01.

Example A13

5-Amino-1-(2.6-dichloro-4-trifluoromethylphenyl-4-ethynyl-3-methoxycarbonylpyrazole To a stirred suspension of potassium carbonate (0.03 g) in methanol (2 ml) was added 5-amino-3-cyano-1-(2,6-dichloro-4-trifluoromethylphenyl)-4-trimethylsilylethynylpyrazole (0.03 g). After 40 hours at 25° C. the reaction mixue was poured into water (10 ml) and extracted with ether (20 ml, x2). The combined organic layers were dried (MgSO$_4$) and evaporated. The residue was purified by recrystallisation from ether/hexane to provide the title compound.

$^1$H NMR (CDCl$_3$) δ: 3.51 (s, 1H), 3.97 (s, 3H), 4.13 (br. s, 2H), 7.78 (s, 2H)

MS (thermospray): M/Z[M]377.0; C$_{14}$H$_8$Cl$_2$F$_3$N$_3$O$_2$ requires 376.99.

Example B1 (Illustrative)

5-Acetamido-3-cyano-1-(2,6-dichloro-4-trifluoromethylphenyl)-4-iodopyrazole

To a stirred solution of 5-amino-3-cyano-1-(2,6-dichloro-4-trifluoromethylphenyl)-4-iodopyrazole (447 mg, the compound of Example A1) in pyridine (5ml) was added dropwise acetyl chloride (0.5 ml). The reaction mixture was stirred at room temperature for 2 days and then heated at 50° C. for 4 hours. The reaction mixture was partitioned between ether (50 ml) and water (50ml), the organic layer was separated, dried (MgSO$_4$) and evaporated.

The crude product was purified by column chromatography on silica gel (40 g) eluted with ether: hexane (10:1) to provide the title compound as a white solid.

MS (thermospray): M/Z[M+NH$_4$]505.4; C$_{13}$H$_6$Cl$_2$F$_3$IN$_4$O+NH$_4$ requires 505.9

Example B2

5-Acetamido-3-cyano-1-(2,6-dichloro-4-trifluoromethylphenyl 4-trimethylsilylethynylpyrazole To a stirred solution of 5-acetamido-3-cyano-1-(2,6-dichloro-4-trifluoromethylphenyl)4-iodopyrazole (80 mg, the compound of Example B1) in triethylamine (5 ml) was added trimethylsilylacetylene (0.1 ml), cuprous iodide (4 mg) and bis(triphenylphosphine)palladium(II) chloride (8 mg). The reaction mixture was heated at 60° C. for 1 hour and then poured into water (20 ml) and ether (20 ml). The organic layer was separated, dried (MgSO$_4$) and evaporated. The crude product was purified by column chromatography on silica gel eluted with ether: hexane (10:1) to provide the title compound as a white solid.

MS (thermospray): M/Z[M+NH$_4$]475.7; C$_{18}$H$_{15}$Cl$_2$F$_3$N$_4$OSi+NH$_4$ requires 476.1

Example B3
5-Acetamido-3-cyano-1-(2,6-dichloro-4-trifluoromethylphenyl)4-ethynylpyrazole To a solution of 5-acetamido-3-cyano-1-(2,6-dichloro-4-trifluoromethylphenyl)4-trimethylsilylethynylpyrazole (20 mg, the compound of Example B2) in methanol (1 ml) was added potassiun carbonate (20 mg). The reaction mixture was stirred at room temperature for 40 minutes and then poured into water (20 ml) and ether (20 ml). The organic layer was separated, dried (MgSO$_4$) and evaporated. The crude product was purified by column chromatography on silica gel eluted with ether to provide the title compound as a white solid.

$^1$H NMR (CDCl$_3$) δ: 2.1 (s, 3H), 3.51 (s, 1H), 7.78 (s, 2H)
MS (thermospray): M/Z[M+NH$_4$]403.9; C$_{15}$H$_7$Cl$_2$F$_3$N$_4$O+NH$_4$ requires 404.0

Example B4
3-Cyano-5-di-(t-butoxycarbonyl)amino-1-(2,6-dichloro-4-trifluoromethlphenyl)-4-ethynyipyrazole To a solution of 5-amino-3-cyano-1-(2,6-dichloro-4-trifluoromethylphenyl)4-ethynylpyrazole (1.3 g, the compound of Example A3) in dimethylformamide (4 ml) and triethylamine (20 ml) was added di-t-butyldicarbonate (0.9 g) and 4-dimethylaminopyridine (5 mg) and the mixture was stirred at room temperature for sixteen hours. Di-t-butyldicarbonate (0.45 g) was then added and stirring continued for two hours. The reaction mixture was then poured into ether (200 ml) and aqueous citric acid solution (200 ml, 20%). The organic layer was separated, dried (MgSO$_4$) and evaporated. The crude product was purified by column chromatography on silica gel eluted with dichloromethane: hexane (1:1) to provide the title compound as a pale yellow solid m.p. 227–8° C.

$^1$H NMR (CDCl$_3$) δ: 1.41 (s, 18H), 3.48 (s, 1H), 7.75 (s, 2H)
Microanalysis—found: C, 50.66, H 3.88, N, 10.27%; C$_{23}$H$_{21}$Cl$_2$F$_3$N$_4$O$_4$ requires C,50.34, H, 3.80, N, 10.04%.

Example B5
3-Cyano-5-di-(t-butoxycarbonyl)amino-1-(2,6-dichloro-4-trifluoromethylphenyl)-4-bromoethynylpyrazole To a solution of 3-cyano-5-di-(t-butoxycarbonyl)amino-1-(2,6-dichloro-4-trifluoromethylphenyl)4-ethynylpyrazole (100 mg, the compound of Example B4) in acetone (10 ml) was added silver nitrate (5 mg) and N-bromosuccinimide (80 mg). The mixture was stirred at room temperature for one hour and then poured into ether (100 ml) and water (100 ml). The organic layer was separated, dried (MgSO$_4$) and evaporated. The crude product was purified by column chromatography on silica gel eluted with dichloromethane to provide the title compound as a pale yellow solid m.p. 130–1° C.

$^1$H NMR(CDCl$_3$) δ: 1.41 (s, 18H), 7.75 (s, 1H)
MS (electrospray): M/Z[M+Na]645.0 ; C$_{23}$H$_{20}$BrCl$_2$F$_3$N$_4$O$_4$+Na requires 645.0

Example B6
5-t-Butoxycarbonylamino-3-cyano-1-(2,6-dichloro-4-trifluoromethylphenyl)-4-bromoethynylpyrazole To a solution of 3-cyano-5-di-(t-butoxycarbonyl)amino-1-(2,6-dichloro-4-trifluoromethylphenyl) 4bromoethynylpyrazole (200 mg, the compound of Example B5) in anhydrous dichloromethane (2 ml) was added dropwise trifluoroacetic acid (0.2 ml). After 30 minutes the reaction mixture was treated with ether (10 ml) and saturated aqueous sodium hydrogen carbonate solution (10 ml). The organic layer was separated, dried (MgSO$_4$) and evaporated to provide the title compound as a white solid m.p. 168–70° C.

$^1$H NMR (CDCl$_3$) δ: 1.38 (s, 9H), 6.23 (s, 1H), 7.75 (s, 2H)
MS (thermospray): M/Z[M+NH$_4$]539.6; C$_{18}$H$_{12}$BrCl$_2$F$_3$N$_4$O$_2$+NH$_4$ requires 540.0

Example B7 (Illustrative)
3-Cyano-1-(2,6-dichloro-4-trifluoromethylphenyl)4iodo-5-(N-pyrroyl)pyrazole A mixture of 5-amino-3-cyano-1-(2,6-dichloro-4-trifluoromethylphenyl)4-iodopyrazole (0.5 g) and 2,5-dimethoxytetrahydrofuran (1 ml) in acetic acid (5 ml) was heated under reflux for 1 hour. The reaction rmixture was poured into diethyl ether (100 ml) and water (100 ml). The organic layer was washed with saturated aqueous potassium bicarbonate solution (50 ml) and dried over MgSO$_4$. Removal of the solvent gave the title compound.

$^1$H NMR (CDCl$_3$) δ: 6.38 (s, 2H), 6.7 (s, 2H), 7.7 (s, 2H)
MS (thermospray): M/Z[M+NH$_4$]513.6; C$_{15}$H$_6$Cl$_2$F$_3$IN$_4$+NH$_4$ requires 513.9.

Example B8
3-Cyano-1-(2,6-dichloro-4-trifluoromethylphenyl)-5-(N-pyrrolyl)4-trimethylsilylethynylpyrazole To a stirred solution of 3-cyano-1-(2,6-dichloro-4-trifluoromethylphenyl)4-iodo-5-(N-pyrrolyl)pyrazole (0.55 g) in triethylamine (1 ml) and dimethylformamide (10 ml) was added trimethylsilylacetylene (1 ml), cuprous iodide (15 mg) and bis(triphenylphosphine)palladium (II) chloride (30 mg). The reaction mixture was heated at 70° C. for 24 hours, and then poured into water (100 ml) and diethyl ether (100 ml). The organic layer was dried over MgSO$_4$ and the solvent was evaporated. The crude product was purified by chromatography on silica gel (50 g), eluting with dichloromethane: hexane (1:1), giving the title compound as a pale brown solid.

Example B9
3-Cyano-1-(2,6-dichloro-4-trifluoromethylphengln-4-ethynyl-5-(N-pyrroIyl)pyrazole To a solution of 3-cyano-1-(2,6-dichloro-4-trifluoromethylphenyl)-5-(N-pyrrolyl)-4-trimethylsilylethynylpyrazole (0.045 g) in dichloromethane (5 ml) was added tetra-n-butylammonium fluoride (0.1 ml, 1M in tetrahydrofuran) dropwise over 5 minutes. The reaction mixture was stirred for 5 minutes and then evaporated to give an oil, which was chromatographed on silica gel (5 g), eluting with dichloromethane. The title compound was obtained as a pale brown solid, m.p. 161–3° C.

$^1$H NMR (CDCl$_3$) δ: 3.44 (s, 1H); 6.3 (m, 2H); 6.77 (m, 2H), 7.74 (s, 2H).
MS (thermospray): M/Z[M+H]394.9; C$_{17}$H$_7$Cl$_2$F$_3$N$_4$+H requires 395.0.

Example B10
3-Cyano-1-(2,6-dichloro-4-trifluoromethylphenyl)-5-dimethylamino-4-ethynylpyrazole To a stirred solution of 5-amino-3-cyano-1-(2,6-dichloro-4-trifluoromethylphenyl)-4-trimethylsilylethynylpyrazole (0.417 g) in tetrahydrofuran (20 ml) was added, portionwise over 5 minutes, sodium hydride (0.1 g of a 60% dispersion in oil). Methyl iodide (0.156 ml) was added dropwise over 2 minutes. After 5 minutes, sodium hydride (0.05 g) and methyl iodide (0.050 ml) were added and stirring was continued for a further 5 minutes. The reaction mixture was then poured into water/diethyl ether. The organic layer was dried over $MgSO_4$ and evaporated to give the title compound as a pale brown solid, m.p. 145–7° C.

$^1$H NMR (CDCl$_3$) δ: 2.83 (s, 6H), 3.42 (s, 1H), 7.78 (s, 2H).

MS (thermospray): M/Z[M+H]373.2; $C_{15}H_9Cl_2F_3N_4$+H requires 373.02.

Example C1
5-Bromo-3-cyano-1-(2,6-dichloro-4-trifluoromethylphenyl)-4-trimethylsilylethynylpyrazole To a stirred solution of 5-amino-3-cyano-1-(2,6-dichloro-4-trifluoromethylphenyl)4-trimethylsilylethynylpyrazole (30 mg, the compound of Example A2) in acetonitrile (0.5 ml) and bromoform (0.5 ml) was added dropwise over five minutes n-butyl nitrite (0.025 ml). The mixture was heated at 70° C. for 30 minutes, then cooled and evaporated. The residue was purified by column chromatography on silica gel (40 g) eluted with dichloromethane: hexane (1:4) to provide the title compound as a white solid m.p. 130° C. (decomp.).

$^1$H NMR (CDCl$_3$) δ: 0.2 (s, 9H), 7.78 (s, 2H)

MS (thermospray): M/Z[M+NH$_4$]497.0; $C_{16}H_{11}BrCl_2F_3N_3Si$+NH$_4$ requires 497.0

Example C2
5-Bromo-3-cyano-1-(2,6-dichloro-4-trifluoromethylphenyl)-4-ethynylpyrazole To a stirred solution of 5-bromo-3-cyano-1-(2,6-dichloro-4-trifluoromethylphenyl)-4-trimethylsilylethynylpyrazole (43 mg, the compound of Example C1) in dichloromethane (1 ml) was added dropwise over five minutes tetra-n-butylammonium fluoride (0.098 ml). Stirring was continued at room temperature for 30 minutes. The reaction mixture was then poured into dichloromethane (10 ml) and water (10 ml). The organic layer was separated, dried (MgSO$_4$) and evaporated. The residue was purified by column chromatography on silica gel (10 g) eluted with dichloromethane : hexane (1:2) to provide the title compound as a pale yellow solid m.p. 134–5° C.

$^1$H NMR (CDCl$_3$) δ: 3.55 (s, 1H), 7.8 (s, 2H)

MS (thermospray): M/Z[M+NH$_4$]425.0; $C_{13}H_3BrCl_2F_3N_3$+NH$_4$ requires 424.9

Example C3
5-Bromo-1-(2,6-dichloro-4-trifluoromethylphenyl)-4-ethyl-3-methoxycarbonylpyrazole To a stirred solution of 5-bromo-3-cyano-1-(2,6-dichloro-4-trifluoromethylphenyl)-4-trimethylsilylethynylpyrazole (100 mg, the compound of Example C1) in methanol (1 ml) was added potassium carbonate (2.9 mg). Stirring was continued at room temperature for 2 hours and then potassium carbonate (3.0 mg) was added. Stirring was continued for a further 4 hours. The reaction mixture was then poured into ether (10 ml) and water (10 ml). The organic layer was separated, dried (MgSO$_4$) and evaporated to provide the title compound as a white solid m.p. 198° C. (decomp.).

$^1$H NMR (CDCl$_3$) δ: 3.6 (s, 1H), 4.09 (s, 3H), 7.79 (s, 2H)

MS (electrospray): M/Z[M+H]441.0; $C_{14}H_6BrCl_2F_3N_2O_2$+H requires 440.9

Example C4
3-Cyano-1-(2,6-dichloro-4-trifluoromethylphenyl)4-trimethylsilylethylpyrazole To a stirred solution of 5-aniino-3-cyano-1-(2,6-dichloro-4-trifluoromethylphenyl)-4-trimethylsilylethynylpyrazole (30 mg, the compound of Example C1) in tetrahydrofuran (10 ml) was added dropwise over five minutes t-butyl nitrite (0.025 ml). The nixture was heated under reflux for 30 minutes, then cooled and evaporated. The residue was purified by column chromatography on silica gel (50 g) eluted with dichloromethane: hexane (1:4) to provide the title compound as a white solid m.p. 128–9° C.

$^1$H NMR (CDCl$_3$) δ: 0.3 (s, 9H), 7.72 (s, 1H), 7.78 (s, 2H)

MS (thermospray): M/Z[M+NH$_4$]419.0; $C_{16}H_{12}Cl_2F_3N_3Si$+NH$_4$ requires 419.0

Example C5
3-Cyano-1-(2,6-dichloro-4-trifluoromethylphenyl)4-ethynlpyrazole

To a stirred solution of 3-cyano-1-(2,6-dichloro-4-trifluoromethylphenyl)-4-trimethylsilylethynylpyrazole (201 mg, the compound of Example C4) in dichloromethane (5 ml) was added dropwise over five minutes tetra-n-butylammonium fluoride (0.55 ml). Stirring was continued at room temperature for 30 minutes. The reaction mixture was then poured into dichloromethane (10 ml) and water (10 ml). The organic layer was separated, dried (MgSO$_4$) and evaporated. The residue was purified by column chromatography on silica gel eluted with dichloromethane : hexane (1:4) to provide the title compound as a pale yellow solid m.p. 130–2° C.

$^1$H NMR (CDCl$_3$) δ: 3.4 (s, 1H), 7.79 (s, 1H +2H)

MS (thermospray): M/Z[M+NH$_4$]347.0; $C_{13}H_4Cl_2F_3N_3$+NH$_4$ requires 347.0

Example C6
4-Bromoethynyl-3-cyano-1-(2,6-dichloro-4-trifluoromethylphenyl)pyrazole To a stirred solution of 3-cyano-1-(2,6-dichloro-4-trifluoromethylphenyl)-4-ethynylpyrazole (100 mg, the compound of Example C5) in acetone (5 ml) was added N-bromosuccinimide (54.9 mg) and silver nitrate (5 mg). Stirring was continued at room temperature for 60 minutes. The reaction mixture was then poured into ether (10 ml) and water (10 ml). The organic layer was separated, dried (MgSO$_4$) and evaporated. The residue was purified by column chromatography on silica gel eluted with dichloromethane: hexane (2: 1) to provide the title compound as a white solid m.p. 166–8° C.

$^1$H NMR (CDCl$_3$) δ: 7.78 (s, 1H), 7.79 (s,2H)

MS (thermospray): M/Z[M+NH$_4$]425.0; $C_{13}H_3BrCl_2F_3N_3$+NH$_4$ requires 424.9

Example C7
4-Chloroethynl-3-cyano-1-(2,6-dichloro-4-trifluoromethylphenyl)pyrazole To a stirred solution of 3-cyano-1-(2,6-dichloro-4-trifluoromethylphenyl)4-ethynylpyrazole (2 g) in acetonitrile (50 ml) was added N-chlorosuccinimde (4 g), and the mixture was heated under refiux for 1 hour, then allowed to stand at room temperature overnight. N-chorosuccinimide (1.2 g) was added and the mixture was heated under refiux for 2 hours. N-chlorosuccinimide (4 g) was added and the mixture was heated under reflux for 4 hours. The reaction mixture was reduced in vacuo and the residue was chromatographed on silica gel, eluting with dichloromethane: hexane (5:1). Suitable fractions were combined and evaporated, and the solid product so obtained was then further purified by HPLC on a 21×250 mm Dynamax™ 0.005 mm ODS reverse-phase column, eluting at 10 ml/minute with acetonitrile: 0.005M aqueous heptanesulphonic acid : methanol (5:4:1). Combination of suitable fractions and evaporation of their non-aqueous components, followed by partitioning between diethyl ether and saturated aqueous sodium bicarbonate solution, drying of the organic layer and evaporation of the solvent, gave the title compound as a white solid, m.p. 1324–4° C.

$^1$H NMR (CDCl$_3$) δ: 7.75 (s, 1H); 7.78 (s,2H).

MS (thermospray): M/Z[M+NH$_4$]380.9. C$_{13}$H$_3$Cl$_3$F$_3$N$_3$+NH$_4$ requires 380.97.

Example C8

3-Cyano-1-(2,6-dichloro-4-trifluoromethylphenl)-4-ethynyl-5-methylthiopyrazole

To a stirred solution of 5-amino-3-cyano-1-(2,6-dichloro-4-trifluoromethylphenyl)4-trimethylsilylethynylpyrazole (0.46 g) in acetonitrile (20 ml) was added dimethyl disulphide (0.108 ml) and the mixture was heated to 50° C. n-Butyl nitrite (0.401 ml) was added and the reaction was warmed to 70° C. for 30 minutes. After cooling to room temperature, tetra-n-butlyammonium fluoride (1.2 ml, 1M in hexane) was added. After 10 minutes the reaction mixture was poured into diethyl ether (50 ml) and water (50 ml). The organic layer was dried (MgSO$_4$) and the solvent removed in vacuo. The residue was chromatographed on silica gel (50 g), eluting with dichloromethane: hexane (2:1). Combination and evaporation of suitable fractions gave a solid which was washed with hexane. The hexane washings were evaporated and the residue was further chromatographed on silica gel (20 g), eluting with diethyl ether: hexane (1:10). Combination and evaporation of suitable fractions gave the title compound as a white solid, m.p. 85–6° C.

$^1$HNMR (CDCl$_3$) δ: 2.56 (s, 3H); 3.51 (s, 1H); 7.79 (s, 2H).

MS (thermospray): M/Z[M+H]376; C$_{14}$H$_6$Cl$_2$F$_3$N$_3$S+H requires 375.97.

Example D1 (Illustrative)

5-Amino-3-cyano-1-(2,6-dichloro-4-trifluoromethoxphenyl)-4-iodopyrazole

To a stirred solution of 5-amino-3-cyano-1-(2,6-dichloro-4-trifluoromethoxyphenyl)pyrazole (4.1716 g) in acetonitrile (20 ml) at room temperature was added N-iodosuccinimide (2.79 g). After 15 minutes the mixture was evaporated to dryness leaving and the residual orange solid taken up in dichloromethane. The solution was washed with water, then brine, then dried (Na$_2$SO$_4$) and evaporated to provide the title compound as a pale orange solid, m.p. 149.5–150.0° C.

$^1$H NMR (CDCl$_3$) δ: 3.95 (br. s, 2H), 7.41 (s, 2H)

MS (thermospray): M/Z[M+H]463.1; C$_{11}$H$_4$Cl$_2$F$_3$IN$_4$O+H requires 462.88

Example D2

5-Amino-3-cyano-1-(2,6-dichloro-4-trifluoromethoxyphenyl-4-trimethylsilylethynylpyrazole To a stirred solution of 5-amino-3-cyano-1-(2,6-dichloro-4-trifluoromethoxyphenyl)-4-iodopyrazole (5.489 g) in dimethylformamide (4 ml) at room temperature was added trimethylsilylacetylene (3.35 ml), cuprous iodide (0.116 g), bis(triphenylphosphine)palladium(II) chloride (0.228 g) and triethylamine (1 ml). The mixture was heated at 60° C. for 2.5 hours. Trimethylsilylacetylene (1.675 ml), cuprous iodide (0.058 g) and bis(triphenylphosphine)palladium(II) chloride (0.114 g) were then added and stirring and heating continued for a further period of one hour. The cooled reaction mixture was diluted with water and extracted with ether. The ether extract was dried (MgSO$_4$) and evaporated to give the crude product which was purified by column chromatography on silica gel eluting with dichloromethane/hexane. Combination and evaporation of suitable fractions followed by recrystallisation of their residue from dichloromethane/hexane provided the title compound as a pale yellow solid m.p. 151.5–152.1° C.

$^1$H NMR (CDCl$_3$) δ: 0.26 (s, 9H), 4.15 (br. s, 2H), 7.42 (s, 2H)

MS (thermospray): M/Z[M+H]433.7; C$_{16}$H$_{13}$Cl$_2$F$_3$N$_4$OSi+H requires 433.03.

Example D3

5-Amino-3-cyano-1-(2,6-dichloro-4-trifluoromethoxyphenyl)-4-ethynylpyrazole

To a stirred solution of 5-amino-3-cyano-1-(2,6-dichloro-4-trifluoromethoxyphenyl)-4-trimethylsilylethynylpyrazole (0.4657 g) in dichloromethane (5 ml) cooled in an ice-water bath was slowly added tetra-n-butylammonium fluoride (1.07 ml of a 1M solution in tetrahydrofuran). After five minutes the ice-water bath was removed. Stirring was continued for ten minutes then the reaction mixture was washed with water. The aqueous layer was washed with dichloromethane. The combined organic layers were washed with brine, dried (Na$_2$SO$_4$) and evaporated to provide the title compound as an oily solid which upon drying in an oven crystallised to a white solid m.p. 175.7–176.1° C.

$^1$H NMR (CDCl$_3$) δ: 3.48 (s, 1H), 4.2 (br. s, 2H), 7.42 (s, 2H)

MS (thermospray): M(Z[M+NH$_4$]377.9; C$_{13}$H$_{15}$Cl$_2$F$_3$N$_4$O+NH$_4$ requires 378.01.

Example D4

3-Cyano-1-(2,6-dichloro-4-trifluoromethoxyphenyl)-4-trimethylsilylethynylprazole To a stirred solution of 5-amino-3-cyano-1-(2,6-dichloro-4-trifluoromethoxyphenyl)-4-trimethylsilylethynylpyrazole (4.0 g) in tetrahydrofuran (50 ml) was added dropwise t-butylnitrite (3.29 ml). The mixture was heated under reflux for 3 hours and then evaporated to dryness. The residue was purified by column chromatography on silica gel eluted with dichworomethane: hexane (3:1). Combination and evaporation of suitable fractions followed by recrystallisation of their residue from hexane provided the title compound as a white solid m.p. 142.3–142.9° C.

$^1$H NMR (CDCl$_3$) δ: 0.3 (s, 9H), 7.39 (s, 2H), 7.70 (s, 1H)

MS (thermospray): M/Z[M+H]418.1; C$_{16}$H$_{12}$Cl$_2$F$_3$N$_3$OSi+H requires 418.02.

Example D5

3-Cyano-1-(2,6-dichloro-4-trifluoromethoxyphenyl)-4-ethynylpyrazole

To a stirred solution of 3-cyano-1-(2,6-dichloro-4-trifiuoromethoxyphenyl)4-trimethylsilylethynylpyrazole (2.691 g) in dichloromethane (25 ml) was added tetra-n-butylammonium fluoride (6.45 ml of a 1M solution in tetrahydrofuran). Stirring was continued for 30 minutes then the reaction mixture was partitioned between water and dichioromethane. The aqueous layer was separated and extracted twice with di-chloromethane. The combined organic layers were washed with brine, dried (Na$_2$SO$_4$) and evaporated. The residue was purified by column chromatography on silica gel eluting with dichloromethane: hexane (1:1). Combination and evaporation of suitable fractions provided the title compound as a white solid m.p. 95.2–96.0° C.

$^1$H NMR (CDCl$_3$) δ: 3.39 (s, 1 H), 7.40 (s, 2H), 7.77 (s, 1H)

MS (thermospray): M/Z[M+NH$_4$]363.1; C$_{13}$H$_4$Cl$_2$F$_3$N$_3$O+NH$_4$ requires 363.0

Example D6
4-Bromoethyyl-3-cyano-1-(2,6-dichloro-4-trifluoromethoxwphenyl)pyrazole To a stirred solution of 3-cyano-1-(2,6-dichloro-4-trifluoromethoxyphenyl)-4-ethynylpyrazole (0.5 g) in acetone (5 ml) was added N-bromosuccinimide (0.258 g) followed by silver nitrate (0.024 g). Stirring was continued for one hour then the reaction mixture was evaporated to dryness. The residue was partitioned between ether and water. The aqueous layer was separated and extracted with ether. The combined organic layers were washed with brine, dried ($Na_2SO_4$) and evaporated. The residue was purified by column chromatography on silica gel eluted with dichloromethane: hexane (1:1). Combination and evaporation of suitable fractions followed by recrystallisation from hexane provided the title compound as a white solid m.p. 123.0–123.8° C.

$^1$H NMR ($CDCl_3$) δ: 7.40 (s, 2H), 7.72 (s, 1H)
MS (thermospray): M/Z[M+NH$_4$]440.9; $C_{13}H_3BrCl_2F_3N_3O+NH_4$ requires 440.9

Example D7 (Ilustrative)
5-Amino-3-cyano-1-(2,6-dichloro-4-trifluoromethylsulphenylphenyl)-4-iodopyrazole To a stirred solution of 5-amino-3-cyano-1-(2,6-dichloro-4-trifluoromethylsulphenylphenyl)pyrazole (10 g) in acetonitrile (50 ml) at room temperature was added N-iodosuccinimide (6.4 g) in acetonitrile (25 ml). After 15 minutes the mixture was evaporated to dryness leaving and the residual buff solid taken up in dichloromethane (300 ml). The solution was washed with water (75 ml, ×3), then brine (50 ml), then dried ($MgSO_4$) and evaporated. Trituration with hexane (100 ml, ×2) to provide the title compound as buff solid m.p. 172–174° C.

$^1$H NMR ($CDCl_3$) δ: 3.96 (br. s, 2H), 7.81 (s, 2H).

Example D8
5-Amino-3-cyano-1-(2,6-dichloro-4-trifluoromethylsulphenylphenyl)4-trimethylsilylethynylpyrazole To a stirred solution of 5-amino-3-cyano-1-(2,6-dichloro-4-trifluoromethylsulphenylphenyl)4-iodopyrazole (10 g) in dimethylformamide (45 ml) at room temperature was added triethylamine (34 ml), trimethylsilylacetylene (6 ml), cuprous iodide (0.4 g), and bis(triphenylphosphine)palladium(II) chloride (0.4 g). The mixture was heated at 75° C. for 6 hours. The cooled reaction mixture was evaporated to dryness and the residue partitioned between water and dichloromethane. The organic layer was separated and washed with water, then brine, and then dried ($Na_2SO_4$) and evaporated to give the crude product which was purified by column chromatography on silica gel (400 g) eluting with dichloromethane. Combination and evaporation of suitable fractions provided an oily solid which was further purified by column chromatography on silica gel (400 g) eluting with dichloromethane/hexane. Combination and evaporation of suitable fractions followed by recrystallisation of their residue from dichloromethane/hexane provided the title compound as a buff solid m.p. 165–169° C.

$^1$H NMR($CDCl_3$) δ: 0.28 (s, 9H), 4.16 (br. s, 2H), 7.8 (s, 2H)
MS (thermospray): M/Z[M+H]448.9; $C_{16}H_{13}Cl_2F_3N_4SSi+H$ requires 449.0.

Example D9
3-Cyano-1-(2,6-dichloro-4-trifluoromethylsulphenylphenl)4-trimethylsilylethynylpyrazole To a stirred solution of 5-amino-3-cyano-1-(2,6-dichloro-4-trifluoromethylsulphenylphenyl)4-trimethylsilylethynylpyrazole (3.0 g) in tetrahydrofiran (18 ml) heated under reflux was added dropwise a solution of t-butylnitrite (2.4 ml) in tetrahydrofuran (7 ml). After completion of the addition the mixture was heated under reflux for one hour and then allowed to cool to room temperature. After standing at room temperature overnight the mixture was evaporated to dryness. The residue was purified by column chromatography on silica gel (100 g) eluting with dichloromethane. Combination and evaporation of suitable fractions followed by recrystailisation of their residue from hexane provided the title compound as a pale yellow solid, m.p. 129–133° C.

$^1$H NMR ($CDCl_3$) δ: 0.29 (s, 9H), 7.72 (s, 1H), 7.8 (s, 2H)
MS (thermospray): M/Z[M+H]434.0; $C_{16}H_{12}Cl_2F_3N_3SSi+H$ requires 433.99.

Example D10
3-Cyano-1-(2,6-dichloro-4-trifuoromethylsulphenMlphenyl)-4-ethynylpyrazole To a stirred solution of 3-cyano-1-(2,6-dichloro-4-trifluoromethylsulphenylphenyl)-4-trimethylsilylethynylpyrazole (2,2 g) in dichloromethane (40 ml) at room temperature was added tetra-n-butylammonium fluoride (6 ml of a 1M solution in tetrahydrofliran). Stirring was continued for 30 minutes then the reaction mixture was concentrated to a small volume and then partitioned between dichloromethane (5 oml) and water (20 ml). The organic layer was separated and washed with water (20 ml), brine (10 ml), dried $Na_2SO_4$) and evaporated. The residue was purified by column chromatography on silica gel (60 g) eluting with dichloromethane. Combination and evaporation of suitable fractions provided the title compound as an off-white glassy solid m.p. 118–119° C.

$^1$H NMR ($CDCl_3$) δ: 3.39 (s, 1H), 7.80 (s+s, 1H+2H)
MS (thermospray): M/Z[M+NH$_4$]379.0; $C_{13}H_4Cl_2F_3N_3O+NH_4$ requires 378.98.

Example D11 (Illustrative)
5-Amino-3-cyano-1-(2,6-dichloro-4-sulphurpentafluorophenyl-4-iodopyrazole To a stirred solution of 5-amnino-3-cyano-1-(2,6-dichloro-4-sulphurpentafluorophenyl)pyrazole (18.95 g) in acetonitrile (100 ml) at room temperature was added N-iodosuccinimide (11.5 g) in four portions over a period of five minutes. After 15 minutes the mixture was evaporated to dryness and the residual solid was treated with dichloromethane and water. The insoluble material was filtered off and dissolved in ethyl acetate. The solution was dried ($Na_2SO_4$) and evaporated to provide the title compound as a buff solid, m.p. 253° C.

$^1$H NMR ($CDCl_3$) δ: 3.94 (br. s, 2H), 7.92 (s, 2H)
MS (thermospray): M/Z[M+NH$_4$]521.9; $C_{10}H_4Cl_2F_5IN_4S+NH_4$ requires 521.88.

Example D12
5-Amino-3-cyano-1-(2,6-dichloro-4-sulphurpentafluorophenyl)4-trimethylsilylethynylpyrazole To a stirred solution of 5-amino-3-cyano-1-(2,6-dichloro-4-sulphurpentafluorophenyl)4-iodopyrazole (5.05 g) in dimethylformamide (5 ml) at room temperature was added cuprous iodide (0.1 g), bis(triphenylphosphine)palladium (II) chloride (0.2 g), trimethylsilylacetylene (2.9 ml) and triethylamine (1 ml). The mixture was heated at 70° C. for 5 hours. The cooled reaction mixture was allowed to stand at room temperature overnight and then poured into water. The precipitate was filtered off and taken up in dichloromethane (50 ml). Following the addition of hexane (100 ml) an oil separated. The supernatant was evaporated to give the crude product which was purified by column chromatography on silica gel (80 g) eluting with dichloromethane : hexane (1:9 then 2:8). Combination and evaporation of suitable fractions followed by recrystallisation of their residue from di-isopropyl ether/hexane provided the title compound as a white microcrystalline solid, m.p. 175° C.

$^1$H NMR (CDCl$_3$) δ: 0.29 (s, 9H), 4.19 (br. s, 2H), 7.94 (s, 2H)

MS (thermospray): M/Z[M+NH$_4$]492.1; C$_{15}$H$_{13}$Cl$_2$F$_5$N$_4$SSi+NH$_4$ requires 492.02.

Example D13

5-Amino-3-cyano-1-(2,6-dichloro-4-sulphurpentafluorophenyl)-4-ethynylpyrazole

To a stirred solution of 5-amino-3-cyano-1-(2,6-dichloro-4-sulphurpentafluorophenyl)-4-trimethylsilylethynylpyrazole (0.4 g) in dichloromethane (5 ml) was added tetra-n-butylammonium fluoride (1.5 ml of a 1M solution in tetrahydrofuran). After one hour tetra-n-butylammonium fluoride (0.5 ml of a 1M solution in tetrahydrofuiran) was added. After three hours the reaction mixture was evaporated to dryness. The residue was purified by column chromatography on silica gel (6.6 g) eluting with hexane:ethyl acetate (9:1, then 4:1, then 2:1) and then ethyl acetate. Combination and evaporation of suitable fractions followed by recrystallisation of their residue from ethyl acetate/hexane provided the title compound as a yellow microcrystalline solid, m.p. 250° C.

$^1$H NMR (d$_6$-Dp MSO) δ: 3.31 (s, 1H), 6.88 (br. s, 2H), 8.47 (s, 2H)

MS (thermospray): M/Z[M+H]403.0 ; C$_{12}$H$_5$Cl$_2$F$_5$N$_4$S+H requires 402.96.

Example E1

5-Amino-3-cyano-1-(2,6-dichloro-4-trifluoromethylphenyl)-4-ethenlpyrazole

To a stirred solution of 5-amino-3-cyano-1-(2,6-dichloro-4trifluoromethylphenyl)-4-iodopyrazole (2 g, the compound of Example A1) in dimethylformamide (10 ml) at room temperature was added vinyltri-n-butyl tin (4.25 g) and tetrakis(triphenylphospine)palladium(0) (300 mg). The mixture was heated at 75° C. for one hour and then cooled and left at room temperature for 60 hours. The reaction mixture was diluted with water and extracted with ether. The organic layer was separated, washed with brine, dried (MgSO$_4$) and evaporated to give the crude product as a black oil (6 g) which was purified by column chromatography on silica gel (200 g) eluted with dichloromethane:hexane (1:1). Combination and evaporation of appropriate fractions gave the title compound as a buff solid m.p. 186–7° C.

$^1$H NMR (CDCl$_3$) δ: 3.85 (s, 2H), 5.41 (d, 1H), 5.7 (d, 1H), 6.52 (dd, 1H), 7.8 (s,2H)

MS (thermospray): M/Z[M+H]347.0 ; C$_{13}$H$_7$Cl$_2$F$_3$N$_4$+H requires 347.0

Example E2

5-Ainino-3-cyano-1-(2,6-dichloro-4-trifluoromethylphenyl)4-tribromoethenylpyrazole To a stirred solution of 5-aniino-3-cyano-1-(2,6-dichloro-4-trifluoromethylphenyl)4-ethynylpyrazole (1035.3 mg, the compound pf Example A3) in ether (20 ml) cooled to −20° C. was added n-butyl lithium (2.52 ml, 2.5M in hexanes) dropwise over 5 minutes. The reaction mixture was then cooled to −78° C. and bromine (0.487 ml) added over 2 minutes. The cooling was discontinued and the reaction mixture allowed to attain room temperature over a period of one hour. The reaction mixture was poured into ether (100 ml) and water (100 ml). The organic layer was separated, dried (MgSO$_4$) and evaporated to give the crude product which was purified by column chromatography on silica gel eluted with dichloromethane:hexane (1:1). Combination and evaporation of appropriate fractions provided the title compound as a white solid m.p. 187° C. (decomp.).

$^1$H NMR (CDCl$_3$) δ: 4.04 (s, 2H), 7.8 (s, 2H)

Microanalysis—found: C, 26.95, H. 0.62, N, 9.55%; C$_{13}$H$_4$Br$_3$Cl$_2$F$_3$N$_4$ requires C,26.75, H, 0.69, N, 9.60%.

Examples E3a and E3b

5-Amino-3-cyano-4-(E-1,2-dibromoethenyl)-1-(2,6-dichloro-4-tifluoromethylphenyl)pyrazole and 5-Amino-3-cyano4-(Z-1,2-dibromoethenpyl)-1-(2,6-dichloro-4-trifluoromethylphenyl)pyrazole To a gently shaken solution of 5-amino-3-cyano-1-(2,6-dichloro-4trifluoromethylphenyl)-4-ethynylpyrazole (100 mg, the compound of Example A3) in ether (1 ml) was added bromine (0.019 ml) dropwise over one minute. The reaction mixture was then evaporated and the product purified by column chromatography on silica gel (10 g) eluted with dichloromethane:hexane (2:1). Combination and evaporation of appropriate fractions provided an approximately 60:40 mixture of the title compounds as a white solid m.p. 138–141° C., which was further purified by HPLC performed on a 21×250 mm Dynamax™ 0.005 mm ODS reverse-phase column, eluting at 10mi/minute with acetonitrile: 0.005 aqueous heptanesulphonic acid:methanol (5:4:1). Suitable fractions were combined and processed by evaporation of the non-aqueous components followed by partition between diethyl ether and saturated aqueous sodium bicarbonate solution. The organic layer was dried and evaporated to give (i) the Z-isomer of the title compound as a buff solid, m.p. 175–6° C.

{$^1$H NMR(CDCl$_3$) δ: 4.04 (br. s, 2H), 6.92 (s,1H), 7.82 (s,2H)}, and (ii) the E-isomer of the title compound as a buff solid, m.p. 169–170° C.

{$^1$H NMR (CDCl$_3$) δ: 3.98 (br. s, 2H), 7.26 (s,1H), 7.8 (s,2H),

MS (thermospray): M/Z[M+H]502.0; C$_{13}$H$_5$Br$_2$Cl$_2$F$_3$N$_4$+NH$_4$ requires 502:8.

Example E4

5-Amino-3-cyano-4-(cyclohex-1-enyl)-1-(2,6-dichloro-4-trifluoromethylphenyl)pyrazole A solution of 5-amino-3-cyano-1-(2,6-dichloro-4-trifluoromethylphenyl) pyrazole (1 g, the compound of Reference Example 1 from EP 295,117) and cyclohexanone (1.6 ml) in acetic acid (5 ml) was stirred and heated at 120° C. overnight under an atmosphere of nitrogen. The cooled reaction mixture was diluted with water and extracted with ethyl acetate and then ether. The combined organic extracts were washed with saturated aqueous sodium hydrogen carbonate solution, then water. After drying (MgSO$_4$), evaporation gave the crude product which was purified by column chromatography on silica gel (50 g) eluted with dichloromethane:hexane (1:2), then dichloromethane:hexane (1:1). Combination and evaporation of appropriate fractions provided the title compound as a white solid m.p. 175–7° C.

$^1$HNMR (CDCl$_3$) δ: 1.7 (m, 2H), 1.8 (m,2H), 2,2 (m, 2H), 2.45 (m, 2H), 3.74 (s, 2H), 5.9 (s, 1H), 7.78 (s, 2H)

Microanalysis—found: C, 50.75, H. 3.07, N, 13.68%; C$_{17}$H$_{13}$Cl$_2$F$_3$N$_4$ requires C,50.89, H, 3.27, N, 13.96%

Example E5

5-Amino-3-cyano-4-(E-1,2-dibromopropen-1-yl)-1-(2,6-dichloro-4-trifluoromethylphenyl)pyrazole To stirred solution of 5-amino-3-cyano-1-(2,6-dichloro-4-trifluoromethylphenyl)-4-(propyn-1-yl)pyrazole (0.045 g)

in ether (2 ml) was added dropwise a solution of bromine (0.02 g) in dichloromethane (1.5 ml). After five minutes at room temperature the reaction mixture was evaporated and the residue purified by column chromatography on silica gel (5 g) eluted with hexane and then dichloromethane: hexane (3:7). Combination and evaporation of appropriate fractions provided the title compound as a white solid.

$^1$H NMR (CDCl$_3$) δ: 2.63 (s, 3H), 3.94 (br. s, 2H), 7.8 (s, 2H)

MS (thermospray): M/Z[M+H]516.2; C$_{14}$H$_7$Br$_2$Cl$_2$F$_3$N$_4$+H requires 516.84.

Example E6
5-Amino-3-cyano-4-(1,2-dibromo-2-phenylethenyl-1-(2,6-dichloro-4-trifluoromethylphenyl)porazole To stirred solution of 5-amino-3-cyano-1-(2,6-dichloro-4-trifluoromethylphenyl)4-phenethynylpyrazole (0.15 g) in dichloromethane (4 ml) was added dropwise a solution of bromine (0.057 g) in dichloromethane (0.25 ml). After 20 minutes at room temperature the reaction mixture was evaporated and the residue purified by column chromatography on silica gel (10 g) eluting with hexane and then hexane containing increasing amounts of dichloromethane. Combination and evaporation of appropriate fractions provided the title compound as a yellow solid, m.p. 211° C.

$^1$H NMR (CDCl$_3$) δ: 4.1 (br. s, 2H), 7.28 (m, 1H), 7.42 (m, 2H), 7.52 (m, 2H), 7.82 (s, 2H)

MS (thermospray): M/Z[M+H]578.7; Cl$_{19}$H$_9$Br$_2$Cl$_2$F$_3$N$_4$+H requires 578.86.

Example E7
5-Amino-3-cyano-4-(1,2-dichloro-2-phenylethenal)-1-(2,6-dichloro-4-trifluoromethylphenfl)pyrazole To stirred solution of 5-amino-3-cyano-1-(2,6-dichloro-4-trifluoromethylphenyl)4-phenethynylpyrazole (0.5 g) in dichloromethane (20 ml) was added dropwise a solution of chlorine (0.085 g) in dichloromethane (5 ml). After 30 minutes at room temperature the reaction mixture was evaporated and the residue purified by column chromatography on silica gel (30 g) eluting with hexane and then hexane containing increasing amounts of dichloromethane. Combination and evaporation of appropriate fractions provided the title compound as an orange solid, m.p 168–172° C.

$^1$H NMR (CDCl$_3$) δ: 3.7 (br. s, 2H), 7.3 (m, 2H), 7.4 (m, 2H), 7.47 (m, 1H), 7.74 (s, 2H)

MS (thermospray) M/Z[M+H]490.8; C$_{19}$H$_9$Cl$_4$F$_3$N$_4$+H requires 490.96.

Example E8
4-(2-Bromo-1,2-dichloroethenyl)-3-cyano-1-(2,6-dichloro-4-trifluoromethoxyphenyl)pyrazole To a stirred solution of 4-bromoethynyl-3-cyano-1-(2,6-dichloro-4-trifluoromethoxyphenyl)pyrazole (0.4 g) in dichloromethane (10 ml) cooled to –78° C. was added a solution of chlorine (0.133 g) in dichloromethane (5 ml). Stirring was continued at –78° C. for two hours and then the reaction mixture was allowed to warm to room temperature. Stirring was continued overnight, then the mixture was evaporated to dryness. The residue was purified by column chromatography on silica gel eluting with dichloromethane: hexane (1:1). Combination and evaporation of suitable fractions followed by recrystallisation from cyclohexane provided the title compound as a white solid, m.p. 143.4–143.80° C.

$^1$H NMR (CDCl$_3$) δ: 7.40 (s, 2H), 7.72 (s, 1H)

MS (thermospray): M/Z[M+H]494.0; C$_{13}$H$_3$BrCl$_4$F$_3$N$_3$O+H requires 493.82.

Example E9
3-Cyano-1-(2,6-dichloro-4-trifluoromethoxyphenyl)4-tribromoethenylprazole To a stirred solution of 3-cyano-1-(2,6-dichloro-4-trifluoromethoxyphenyl)4-ethynylpyrazole (0.5 g) in tetrahydrofuran (20 ml) cooled to –45° C. was added n-butyllithium (0.876 ml of a 2.5M solution in hexane) at such at rate that the temperature was maintained below –40° C. After cooling to –78° C. stirring was continued for twenty minutes then bromine (0.187 ml) was added dropwise. Stirring was continued for 15 minutes then the reaction mixture was allowed to warm to room temperature and stirring continued for a further 15 minutes. The reaction mixture was then partitioned between ether and water. The aqueous layer was separated and extracted twice with ether. The combined organic layers were washed with brine, dried (Na$_2$SO$_4$) and evaporated. The residue was purified by column chromatography on silica gel eluted with dichloromethane : hexane (1:2). Combination and evaporation of suitable fractions followed by recrystallisation from hexane provided the title compound as a white solid m.p. 155.9–156.2° C.

$^1$H NMR (CDCl$_3$) δ: 7.42 (s, 2H), 7.82 (s, 1H)

MS (thermospray): M/Z[M+NH$_4$]598.7; C$_{13}$H$_3$BrCl$_2$F$_3$N$_3$O+NH$_4$ requires 598.75.

Example E10
5-Amino-3-cyano-1-(2,6-dichloro-4-sulphurpentafluorophenl)-4-ethenylpyrazole To a stirred, degassed solution of 5-amino-3-cyano-1-(2,6-dichloro-4-sulphurpentafluorophenyl)-4-iodopyrazole (5.05 g) and tetrakis(triphenylphospine)palladium(0) (0.175 g) in dimethylformamide (32 ml) at room temperature was added yinyltri-n-butyltin (4.5 ml). The mixture was heated to 70° C. over 30 minutes and then maintained at 70° C. for one hour. Tetrakis(triphenylphospine)palladium(0) (0.175 g) and yinyltri-n-butyltin (4.5 ml) were added and heating continued for a further hour. The reaction mixture was evaporated and the residue partitioned between water and ether. The aqueous layer was extracted with ether. The combined organic layers were washed with brine, dried (MgSO$_4$) and evaporated to give the crude product as a brown paste. Trituration with hexane yielded a brown solid which was taken up in ethyl acetate and filtered. The filtrate was evaporated and its residue recystallised from toluene to give the title compound as a buff solid, m.p. 227–228° C.

$^1$H NMR (CDCl$_3$) δ: 3.86 (s, 2H), 5.41 (d, 1H), 6.5 (d, 1H), 6.5 (dd, 1H), 7.92 (s, 2H)

MS (thermospray): MNZ[M+H]405.1 ; C$_{12}$H$_7$Cl$_2$F$_5$N$_4$S+H requires 404.98.

Example E11 (Illustrative)
3-Cyano-1-(2,6-dichloro-4-sulphurpentafluorophenyl)-4-iodopyrazole To a stirred solution of 5-an-iino-3-cyano-1-(2,6-dichloro-4-sulphurpentafluorophenyl)4-iodopyrazole (2.5 g) in tetrahydrofuran (35 ml) heated under reflux was added dropwise over thirty minutes a solution of t-butyl nitrite (3.1 g) in tetrahydrofuran (15 ml). The reaction mixture was then evaporated and the residue recrystallised from isopropanol to provide the title compound as a pinkish solid m.p. 179–180° C.

$^1$HNMR (CDCl$_3$) δ: 7.66 (s, 1H), 7.9 (s, 2H)

MS (thermospray): M(Z[M+NH$_4$]506.4; C$_{10}$H$_3$Cl$_2$F$_5$IN$_3$S+NH$_4$ requires 506.87.

Example E12
3-Cyano-1-(2,6-dichloro-4-sulphurpentafluorophenyl)-4-ethenylpyrazole To a stirred, degassed solution of 3-cyano-1-(2,6-dichloro-4-sulphurpentafluorophenyl)4-iodopyrazole (1.23 g) and tetrakis(triphenylphospine)palladium(0) (0.09 g) in dimethylformamide (32 ml) at room temperature was added vinyltri-n-butyltin (4.2 ml). The mixture was heated at 70° C. for 1.5 hours. The reaction mixture was evaporated and the residue triturated with hexane. The resulting solid was taken up in dichworomethane and applied to a column of silica gel (60 g). Elution with hexane and then hexane : dichloromethane (4:1) gave, after combination and evaporation of appropriate fractions, the title compound as a white solid, m.p. 156° C.

$^1$H NMR (CDCl$_3$) δ: 5.5 (d, 1H), 5.95 (d, 1H), 6.63 (dd, 1H), 7.77 (s, 1H), 7.92 (s, 2H)

MS (thermospray): M/Z[M+NH$_4$]406.8; C$_{12}$H$_6$Cl$_2$F$_5$N$_3$S+NH$_4$ requires 406.99.

Example F1 (Illustrative)
3-Cyano-1-(2,6-dichloro 4trifluoromethylphenyi)4-iodopyrazole To a stirred solution of 5-amino-3-cyano-1-(2,6-dichloro trifluoromethylphenyl)-4-iodopyrazole (90 g) in tetrahydrofulran (720 ml) heated to 65° C. was added t-butyl nitrite (144 ml) over a period of 0.5 hours. Stirring and heating were continued for 3 hours. The cooled reaction mixture was evaporated and the residue was crystallised from n-propanol to give the title compound as a white solid, m.p. 83–4° C.

$^1$H NMR (CDCl$_3$) δ: 7.7 (s, 1H); 7.79 (s, 2H).

MS (thermospray): M/Z[M+NH$_4$]448.8. C$_{11}$H$_3$Cl$_2$F$_3$N$_3$I+NH$_4$ requires 448.9.

Example F2
3-Cyano-1-(2,6dichloro-4trifluoromethylphenyl)-4-ethenylpyrazole

A solution of 3-cyano-1-(2,6-dichloro-4-trifluoromethylphenyl)4-iodopyrazole (58 g) in dimethylformamide (350 ml) containing yinyltri-n-butyltin (116 ml) and tetrakis(triphenylphosphine)palladium(0) (3.5 g) was stirred at 75° C. for 3 hours. The reaction nixture was poured into water (600 ml) and ether (600 ml). The organic layer was washed with water (5 times), brine (700 ml) and dried over sodium sulphate. Removal of the solvent in vacuo was followed by recrystallisation of the residue from propan-2-ol, to give the title compound as a pale brown solid, m.p. 75–6° C.

$^1$H NMR (CDCl$_3$) δ: 5.5 (d, 1H); 5.94(d, 1H); 6.64 (dd, 1H); 7.64(s, 1H); 7.77(s, 1H ).

MS (thermospray): M/Z[M+NH$_4$]349.5. C$_{13}$H$_6$Cl$_2$F$_3$N$_3$+NH$_4$ requires 349.02.

Example F3(Illustrative)
3-Cyano-1-(2,6-dichloro-4-trifuoromethylphenyl)-4-formylprazole A solution of 3-cyano-1-(2,6 dichloro-4-trifluoromethylphenyl)-4-ethenylpyrazole (0. 1 g), N-methylmorpholine oxide (0.005 g), osmium tetroxide (0.05 ml of a 2.5% solution in t-butanol) in water (5 ml) and acetone (45 ml) was stirred at room temperature for 16 hours. Sodium metaperiodate (0.005 g) was added and stirring was continued for 16 hours. The reaction mixture was reduced in vacuo and the residue was partitioned between diethyl ether and aqueous sodium bicarbonate solution. The aqueous layer was separated and extracted with diethyl ether. The combined ether extracts were dried over sodium sulphate and evaporated. The residue was purified by column chromatography on silica gel (5 g), eluting with dichloromethane, giving the title compound as abeige solid, m.p.167.5–168.5° C.

$^1$H NMR(CDCl$_3$) δ: 7.8 (s,2H); 8.18(s,1H); 10.08(s,1H).

MS(thermospray):M/Z[M+NH$_4$]351.3. C$_{12}$H$_4$Cl$_2$F$_3$N$_3$O+NH$_4$ requires 351.0.

Example F4
4(2,2-Dibromoethenyl-3-cyano-1-(2,6-dichloro-4-trifuoromethyphenyl)-pyrazole To a stirred solution of triphenylphosphine (0.983 g) in dry dichloromethane (50 ml) at 0° C. under dry nitrogen was added carbon tetrabromide (0.497 g). The mire was stirred for 5 minutes and then 3-cyano-1-(2,6-dichloro-4-trifluoromethylphenyl)4formylpyrazole (0.25 g) was added. The miture was allowed to warm to room temperature and strring was continued for 1 hour. The reaction mixture was evaporated and the residue was purified by column chromatography on silica gel, eluting with dichloromethane, giving the title compound as a white solid, m.p.109–110° C.

$^1$H NMR (CDCl$_3$) δ: 7.48(s, 1H); 7.76(s, 2H); 8.34(s, 1H).

MS(thermospray):M/Z[M+H]487.2. C$_{13}$H$_4$Br$_2$Cl$_2$F$_3$N$_3$+H requires 487.8.

Example F5a
4Z-1,2-Dibromoethenyl)-3-cyano-1-(2,6-trifuoromethylphenyl)-pyrazole and

Example F5b
4-(E-1,2-Dibromoethenyl)-3-cyano-1-(2,6-dichloro-4-triromethylphenyl)-pyrazole To a stirred solution of 5-amino4-dibromoethenyl-3-cyano-1-(2,6-dichloro-4-trifluoromethylphenyl)pyrazole (E/Z mixture) (0.3 g) in tetrahydrofuran (2 ml) was added t-butyl nitrite (0.21 ml) and the mixture was heated at 65° C. for 1 hour. The reaction mure was evaporated and the residue chromatographed on silica gel (20 g), eluting with hexane and then hexane: dichloromethane (1:3). Suitable fractions were combined and reduced in vacuo, and further purified by HPLC on a 21×250 mm Dynamax™ 0.005 mm ODS reverse-phase column, eluting at 11 ml/minute with acetonitrile: water (3:2), to give (i) 4-(Z-1,2-dibromoethenyl)-3cyano-1-(2,6-dichloro-4-trifluoromethylphenyl)pyrazole as a white solid, m.p. 88–90° C., {$^1$H NMR (CDCl$_3$) δ: 7.7 (s, 1H); 7.8 (s, 2H); 7.87 (s, 1H) MS(thermospray):M/Z[M+NH$_4$]504. C$_{13}$H$_4$Br$_2$Cl$_2$F$_3$N$_3$+NH$_4$ requires 504.8.} and (ii) 4-E-1,2-dibromoethenyl)3-cyano-1-(2,6-dichloro-4-trifluoromethylphenyl)pyrazole as a white solid, m.p. 119° C., {$^1$H NMR (CDCl$_3$) δ: 7.0 (s, 1H); 7.8 (s, 2H); 7.98 (s, 1H) MS(thermospray):M/Z[M+NH$_4$]504.3. C$_{13}$H$_4$Br$_2$Cl$_2$F$_3$N$_3$+NH$_4$ requires 504.8.}

Example F6
3-Cyano4-(2,2-dichloroethenyl)-1-(2,6-dichloro-4-trifluoromethylphenyl)pyrazole A solution of triphenylphosphine (0.983 g) and carbon tetrachloride (0.145 ml) in anhydrous dichloromethane (5 ml) at 0° C. was stirred for 5 minutes. 3-Cyano-1-(2,6-dichloro-4-trifluoromethylphenyl)-4-formylpyrazole (0.25 g) was then added and the mixture was heated under reflux for 5 hours and then evaporated. The residue was purified by column chromatography on silica gel eluting with dichloromethane. Combination and evaporation of suitable fractions gave the title compound as a white solid, m.p. 99–101° C.

$^1$H NMR (CDCl$_3$) δ: 6.9 (s, 1H), 7.8 (s, 2H), 8.2 (s, 1H).

MS (thermospray): M/Z[M+NH$_4$]417.0; C$_{13}$H$_4$Cl$_4$F$_3$N$_3$+NH$_4$ requires 416.95.

Example F7
3-Cyano-1-(2,6-dichloro-4-trifluoromethylphenyl)4-(2,2-difluoroethenyl)pyrazole 3-Cyano-1-(2,6-dichloro-4-trifluoromethylphenyl)-4-formylpyrazole (1.3 g), triphenylphosphine (5.1 g), dibromodifluoromethane (2 g) and dichloromethane (50 ml) were placed in a stainless steel bomb and heated and stirred at 70° C. for 3 hours. The reaction mixtiure was evaporated and the residue was purified by column chromatography on silica gel eluting with dichloromethane: hexane (9:1). Combination and evaporation of suitable fractions gave the title compound as a white solid, m.p. 75–77° C.

$^1$H NMR (CDCl$_3$) δ: 5.43 (d, 1H), 7.7 (s, 1H), 7.79 (s, 2H).

MS (thermospray): M/Z[M+NH$_4$]368.0; C$_{13}$H$_4$Cl$_2$F$_5$N$_3$+NH$_4$ requires 368.0

Example F8a and F8b
4-(E-2-Chloro-3,3,3-trifluoropropenyl)-3-cyano-1-(2,6-dichloro-4-trifluoromethylphenyl)-pyrazole and
4-(Z-2-Chloro-3,3,3-trifluoropropenyl)-3-cyano-1-(2,6-dichloro-4-trifluoromethylphenyl)-pyrazole A stirred solution of 3-cyano-1-(2,6-dichloro-4-trifluoromethylphenyl)4-formylpyrazole (0.75 g), 1,1,1-trichloro-2,2,2-trifluoroethane (0.54 ml), acetic anhydride (0.32 ml) in dimethylformamide (2 ml) containing zinc powder (0.734 g) was heated at 50° C. for 3 hours. The cooled reaction mixture was diluted with water (20 ml) and extracted with ether (50 ml, ×3). The combined organic layers were dried and evaporated. The residue was purified by column chromatography on silica gel eluting with dichloromethane. Combination and evaporation of suitable fractions which were further purified by reversed phase performance chromatography on C18 silica eluting with methanol: acetonitrile: PIC B7 buffer (10:65:35). Appropriate fractions were pooled, partially evaporated and partitioned between ether and water. The organic layer was separated, dried and evaporated to give: 4-(E-2-chloro-3,3,3-trifluoropropenyl)-3-cyano-1-(2,6-dichloro-4-trifluoromethylphenyl)pyrazole as a white solid, m.p.108–110° C., $^1$H NMR (CDCl$_3$) δ: 7.1 (s, 1H), 7.8 (s, 2H), 7.83 (s, 1H).

MS (thermospray): M/Z[M+H]434; C$_{14}$H$_4$Cl$_3$F$_6$N$_3$+H requires 433.94; and 4-(Z-2-chloro-3,3,3-trifluoropropenyl)-3-cyano-1-(2,6-dichloro-4-trifluoromethylphenyl)pyrazole as a white solid, m.p. 125–126° C., $^1$H NMR (CDCl$_3$) δ: 7.36 (s, 1H), 7.8 (s, 2H), 8.42 (s, 1H), MS (thermospray): M/Z[M+NH$_4$]434; C$_{14}$H$_4$Cl$_3$F$_6$N$_3$+H requires 433.94.

Example F9a and F9b
4-(E-2-Bromo-3,3,3-trifluoropropenyl)-3-cyano-1-(2,6-dichloro-4-trifluoromethylphenyl)pyrazole and
4-(Z-2-Bromo-3,3,3-trifluoropropenyl)-3-cyano-1-(2,6-dichloro-4-trifluoromethylphenyl)pyrazole A stirred solution of 3-cyano-1-(2,6-dichloro-4-trifluoromethylphenyl)4-formylpyrazole (0.5 g), 1,1,1-tribromo-2,2,2-trifluoroethane (0.96 g), acetic anhydride (0.3 ml) in dimethylformamide (2 ml) containing zinc powder (0.49 g) was heated at 50° C. for 12 hours. The cooled reaction mixture was diluted with dichloromethane (20 ml) and washed twice with water (10 ml). The organic phase was dried and evaporated. The residue was purified by column chromatography on silica gel eluting with dichloromethane. Combination and evaporation of suitable fractions gave: 4-(E-2-bromo-3,3,3-trifluoropropenyl)-3-cyano-1-(2,6-dichloro-4-trifluoromethylphenyl)pyrazole as a white solid.

$^1$H NMR (CDCl$_3$) δ: 6.58 (s, 1H), 7.8 (s, 2H), 7.97 (s, 1H); and 4-(Z-2-bromo-3,3,3-trifluoropropenyl)-3-cyano-1-(2,6-dichloro-4-trifluoromethylphenyl)pyrazole as a white solid, m.p. 125–126° C.

$^1$H NMR (CDCl$_3$) δ: 7.68 (s, 1H), 7.8 (s, 2H), 8.62 (s, 1H).

MS (thermospray): M/Z[M+NH$_4$]494.6; C$_{14}$H$_4$BrCl$_2$F$_6$N$_3$+NH$_4$ requires 494.92

Example F10
3-Cyano-1-(2,6-dichloro-4-trifuoromethylphenyl)-4-Z-2-fluoro-3,3,3-trifluoropropen-1-yl)pyrazole 3-Cyano-1-(2,6-dichloro-4-trifluoromethylphenyl)-4-formylpyrazole (1.25 g), acetic anhydride (0.5 ml), dimethylformamide (50 ml) and zinc powder (1.2 g) were placed in a stainless steel bomb and cooled to −40° C. 1,1-Dichloro-1,2,2,2-tetrafluoroethane (1.6 g) was added and the bomb sealed then heated and stirred at 70° C. for 6 hours. The reaction mixture was partitioned between ether and water. The organic phase was separated, dried and evaporated. The residue was purified by column chromatography on silica gel eluted with dichloromethane. Combination and evaporation of suitable fractions gave the title compound as a white solid.

$^1$H NMR (CDCl$_3$) δ: 6.57 (d, 1H), 7.8 (s, 2H), 8.05 (s, 1H).

Example F11
3-Cyano-4-(trans-2-cyanoethenyl)-1-(2,6-dichloro-4-trifluoromethylphenyl)pyrazole A mixture of 3-cyano-1-(2,6-dichloro-4-trifluoromethylphenyl)-4-iodopyrazole (0.864 g), acrylonitrile (0.264 g), triethylamine (0.4 ml), palladium acetate (0.04 g) and dimethylformamide (10 ml) were stirred under an atmosphere of nitrogen at 70° C. for 24 hours. The reaction mixture was evaporated and the residue partitioned between water and dichloromethane. The organic layer was separated, washed with water, brine, then dried (Na$_2$SO$_4$) and evaporated. The residue was purified by column chromatography on silica gel (40 g) eluted with dichloromethane. Combination and evaporation of suitable fractions gave the title compound as a white solid m.p. 144–145° C.

$^1$H NMR(CDCl$_3$) δ: 6.19 (d, 1H), 7.34 (d, 1H), 7.8 (s, 2H), 7.81 (s, 1H).

MS (thermospray): M/Z[M+NH$_4$]373.8; C$_{14}$H$_5$Cl$_2$F$_3$N$_4$+NH$_4$ requires 374.02.

Example F12
3-Cyano-1-(2,6-dichloro-4-trifuoromethylphenyl)-4-trifluoromethylethynylpyrazole To a stirred solution of trifluoropropyne (0.66 g) in anhydrous tetrahydrofuran (10 ml) at −78° C. was added n-butyllithium (3.125 ml of 2.5M solution in hexane) maintaining the temperature below −70° C. After 30 minutes zinc chloride (44 ml of a 0.5M solution in tetrahydrofuran) was added and the mixture was allowed to warm to room tempaerature over three hours. After cooling to 0° C. bis(triphenylphosphine)palladium chloride (0.12 g) and 3-cyano-1-(2,6-dichloro-4-trifiluoromethylphenyl)4-iodopyrazole (1.5 g) were added and the mixture heated under reflux for 6 hours. The cooled mixture was then partitioned between ether and water. The organic phase was separated, dried and evaporated. The residue was purified by column chromatography on silica gel eluted with dichloromethane: hexane (3:7). Combination and evaporation of suitable fractions gave the title compound as a pale yellow solid m.p. 121–123° C.

$^1$H NMR (CDCl$_3$) δ: 7.8 (s, 2H), 7.94 (s, 1H).
MS (thermospray): MZ[M+NH$_4$]414.9 ; C$_{14}$H$_3$Cl$_2$F$_6$N$_3$+NH$_4$ requires 414.80.

Example F13
4-(1,2-Dibromo-3,3,3-trifluoropropenyl)-3-cyano-1-(2,6-dichloro-4-trifluoromethylphenyl)pyrazole To a stirred solution of 3-cyano-1-(2,6-dichloro-4-trifiluoromethylphenyl)4-trifluoromethylethynylpyrazole (0.11 g) in ether (1 ml) was added bromine (0.015 ml). After 24 hours the reaction mixture was partitioned between ether (10 ml) and water (10 ml). The organic phase was separated, dried and evaporated to give the title compound (as an isomeric mixture) as an off-white solid m.p. 119–121° C.

$^1$H NMR (CDCl$_3$) δ: 7.8 (s, 2H), 7.9 & 7.94 (s & s, 1H).
MS (thermospray): M/Z[M+NH$_4$]556.0; C$_{14}$H$_3$Br$_2$Cl$_2$F$_6$N$_3$+NH$_4$ requires 555.8.

Example F14a and F14b
3-Cyano-1-(2,6-dichloro-4-trifluoromethylphenyl)-4-tribromoethenylpyrazole and
5-bromo-3-cyano-1-(2,6-dichloro-4-trifluoromethylphenyl)-4-tribromoethenylpyrazole To a stirred solution of 3-cyano-1-(2,6-dichloro-4-trifluoromethylphenyl)-4-ethynylpyrazole (0.25 g) in tetrahydrofuran (10 ml) at −20° C. was added n-butyllithium (0.455 ml of 2.5M solution in hexane). After 5 minutes the mixture was cooled to −78° C. and brorine (0.0975 ml) was added dropwise. The mixture was allowed to warm to room temperature over 10 minutes and then poured into water (20 ml) and ether (10 ml). The organic layer was separated, dried and evaporated. The residue was purified by column chromatography on silica gel (10 g) eluted with hexane and then hexane: dichloromethane (2:3). Combination and evaporation of suitable fractions gave the title compounds as white crystalline solids, m.p.s 163–163.5° C. and 136–139° C. respectively.

$^1$H NMR (CDCl$_3$) δ: 7.8 (s, 2H), 7.85 (s,1H)
MS (thermospray): M/Z[M+NH$_4$]582.4; C$_{13}$H$_3$Br$_3$Cl$_2$F$_3$N$_3$+NH$_4$ requires 582.72. and $^1$H NMR (CDCl$_3$) δ: 7.8 (s, 2H)
MS (thermospray): M/Z[M+NH$_4$]660.7; C$_{13}$H$_2$Br$_4$Cl$_2$F$_3$N$_3$+NH$_4$ requires 660.67.

Example F15
3-Cyano-1-(2,6-dichloro-4-trifluoromethylphenyl)4-trichloroethenalpyrazole To a stirred solution of 3-cyano-1-(2,6-dichloro-4-trifluoromethylphenyl)4-chloroethynylpyrazole (0.25 g) in dichloromethane (10 ml) was added chlorine (0.049 g) and the mixture left overnight. Chlorine (0.049 g) was added and the mixture again left overnight. The mixture was evaporated and the residue was purified by column chromatography on silica gel (50 g) eluted with hexane: ether: dichloromethane (8:1:1). Combination and evaporation of suitable fractions gave the title compound as a white solid, m.p. 122–124° C.

$^1$H NMR (CDCl$_3$) δ: 7.79 (s, 2H), 7.93 (s, 1H)
MS (thermospray): M/Z[M+NH$_4$]450.8; C$_{13}$H$_3$Cl$_5$F$_3$N$_3$+NH$_4$ requires 450.91.

Example F16
3-Cyano4-(E-1,2-dibromopropenyl)-1-(2,6-dichloro-4-trifluoromethylphenyl)pyrazole To a stirred solution of 5-amino4-(E-1,2-dibromopropenyl)-3-cyano-1-(2,6-dichloro-4-trifluoromethylphenyl)pyrazole (0.06 g) in tetrahydrofuran (1.5 ml) was added t-butyl nitrite (0.05 ml). The reaction mixture was heated at 60° C. for two hours. The reaction mixture was then evaporated and the residue was purified by column chromatography on silica gel (5 g) eluted with hexane: dichloromethane (100:0 to 20:70). Combination and evaporation of suitable fractions gave the title compound as a white solid, m.p. 134–135° C.

$^1$H NMR (CDCl$_3$) δ: 2.64 (s, 3H), 7.78 (s, 1H), 7.79 (s, 2H)
MS (thermospray): M/Z[M+NH$_4$]518.6; C$_{14}$H$_6$Br$_2$Cl$_2$F$_3$N$_3$+NH$_4$ requires 518.86.

Example F17
4-(2-Bromo-1,2-dichloroethenyal-3-cyano-1-(2,6-dichloro-4-trifluoromethylphenyl)-pyrazole To a stirred solution of 4-bromoethynyl-3-cyano-1-(2,6-dichloro-4-trifluoromethylphenyl)pyrazole (0.2 g) in dichloromethane (5 ml) cooled to −78° C. was added chlorine (2.17 ml of a 0.255M solution in dichloromethane). The reaction mixture was allowed to warm to room temperature. After two hours chlorine (2.17 ml of a 0.255M solution in dichloromethane) was added and stirring was continued for two days then the mixture was evaporated to dryness to provide the title compound as a white solid m.p. 128–131° C.

$^1$H NMR (CDCl$_3$) δ: 7.80 (s, 2H), 7.92 (s, 1H)
MS (thermospray): M/Z[M+NH$_4$]495.1; C$_{13}$H$_3$BrCl$_4$F$_3$N$_3$+NH$_4$ requires 494.86.

Example F18
4-(2-Chloro-1,2-dibromoethenyl)-3-cyano-1-(2,6-dichloro-4-trifluoromethylphenyl)-pyrazole To a stirred solution of 4-chloroethynyl-3-cyano-1-(2,6-dichloro-4-trifluoromethylphenyl)pyrazole (0.1203 g) in anhydrous dichloromethane (3 ml) was added bromine (0.017 ml). Stirring was continued overnight then the mixture was evaporated to dryness to provide after recrystallisation from hexane the title compound as a white solid m.p. 135–138° C.

$^1$H NMR (CDCl$_3$) δ: 7.80 (s, 2H), 7.83 (s, 1H)
MS (thermospray): M/Z[M+NH$_4$]538.8; C$_{13}$H$_3$Br$_2$Cl$_3$F$_3$N$_3$+NH$_4$ requires 538.81.

Example F19 (Illustrative)
4-Acetyl-5-amino-3-cyano-1-(2,6-dichloro-4-trifluoromethylphenyl)pyrazole To a solution of 5-amino-3-cyano-1-(2,6-dichloro-4-trifluoromethylphenyl)4-ethynylpyrazole (0.345 g) in acetonitrile (5 ml) was added p-toluenesulphonic acid (0.5 g) and the mixture was stirred at room temperature for 2 hours and then poured into water (100 ml) and ether (100 ml). The organic layer was separated, washed with saturated aqueous sodium hydrogen carbonate solution (50 ml), brine (50 ml), dried (Na$_2$SO$_4$) and evaporated. The residue was purified by column chromatography on silica gel (40 g) eluted with dichloromethane: hexane (10:1). Combination and evaporation of suitable fractions gave the title compound as a white crystalline solid, m.p. 200–201° C.

$^1$H NMR (CDCl$_3$) δ: 2.65 (s, 3H), 5.83 (br. s, 2H), 7.82 (s, 2H).
MS (thermospray): M/Z[M+NH$_4$]380.4; C$_{13}$H$_7$Cl$_2$F$_3$N$_4$O+NH$_4$ requires 380.03.

Example F20 (Illustrative)
4-Acetyl-3-cyano-1-(2,6-dichloro-4-trifluoromethylphenyl)pyrazole To a solution of 4-acetyl-5-amnino-3-cyano-1-(2,6-dichloro-4-trifluoromethylphenyl)-pyrazole (0.4 g) in tetrahydrofuiran (2 ml) was added dropwise t-butylnitrite (0.0262 ml). The mixture was heated under reflux for 30 minutes. The reaction mixture was applied to a silica gel (1 g) column and eluted with tetrahydrofuran to provide the title compound as white solid m.p. 166–168° C.

$^1$H NMR (CDCl$_3$) δ: 2.67 (s, 3H), 7.8 (s, 2H), 8.12 (s, 1H).

MS (thermospray): M/Z[M+NH$_4$]365.0; C$_{13}$H$_6$Cl$_2$F$_3$N$_3$O+NH$_4$ requires 365.02.

Example F21

3-Cyano-1-(2,6-dichloro-4-trifluoromethylphenyl)4-(1-methyl-2,2-dibromoethenyl)pyrazole A solution of triphenylphosphine (0.94 g) and carbon tetrabromide (0.6 g) in anhydrous dichloromethane (30 ml) at 0° C. was stirred for 5 minutes. 4-Acetyl-3-cyano-1-(2,6-dichloro- 4-trifluoromethylphenyl)pyrazole (0.25 g) was then added and the mixture was heated under reflux for 6 hours and then evaporated. The residue was purified by column chromatography on silica gel eluted with dichloromethane. Combination and evaporation of suitable fractions gave the title compound as a pale pink solid, m.p. 119–122° C.

$^1$H NMR (CDCl$_3$) δ: 2.35 (s, 3H), 7.79 (s+s, 1H +2H).

MS (thermospray): M/Z[M+NH$_4$]518.7; C$_{14}$H$_6$Br$_2$Cl$_2$F$_3$N$_3$+NH$_4$ requires 518.86.

Example F22

3-Cyano-1-(2,6-dichloro-4-trifluoromethylphenyl)4-(1-methyl-2,2-difluoroethenyl)pyrazole 4-Acetyl-3-cyano-1-(2,6-dichloro-4-trifluoromethylphenyl)pyrazole (0.5 g), triphenylphosphine (1.884 g), dibromodifluoromethane (0.33 ml) and dichloromethane (50 ml) were placed in a stainless steel bomb and heated and stirred at 90° C. for 12 hours. The reaction mixtiure was evaporated and the residue was purified by column chromatography on silica gel eluted with dichloromethane. Combination and evaporation of suitable fractions gave the title compound as a white solid, m.p. 66–68° C.

$^1$H NMR(CDCl$_3$) δ: 2.15 (m, 3H), 7.68 (s, 1H), 7.8 (s, 2H).

MS (thermospray): M/Z[M+NH$_4$]398.9; C$_{14}$H$_6$Cl$_2$F$_5$N$_3$+NH$_4$ requires 399.02.

Example F23 (Illustrative)

5-Chloro-3-cyano-1-(2,6-dichloro-4-trifluoromethylphenyl)-4-iodopyrazole

To a stirred solution of 5-amino-3-cyano-1-(2,6-dichloro-4-trifluoromethylphenyl)-4-iodopyrazole (1 g) in acetonitrile (15 ml) at 0° C. was added dropwise nitrosyl chloride (2.7 ml of a ~1M solution in dichloromethane). The reaction mixture was heated under reflux for 10 minutes. The reaction mixture was then evaporated and the residue was purified by column chromatography on silica gel eluted with hexane: toluene (2:1) and then toluene. Combination and evaporation of suitable fractions gave the title compound as a pale orange solid, m.p. 115.7–116.3° C.

$^1$H NMR (CDCl$_3$) δ: 7.8 (s, 2H)

MS (thermospray): M/Z[M+H]466.0 ; C$_{11}$H$_2$Cl$_3$F$_3$IN$_3$+H requires 465.84.

Example F24

5-Chloro-3-cyano-1-(2,6-dichloro-4-trifluoromethylphenyl)-4-ethenylpyrazole

To a stirred solution of 5-chloro-3-cyano-1-(2,6-dichloro-4-trifluoromethylphenyl)4-iodopyrazole (6 g) in dimethylformamide (75 ml) at room temperature was added and tetrakis(triphenylphospine)palladium(0) (0.448 g). After 5 minutes yinyltri-n-butyltin (11.3 ml) was added dropwise and the mixture was heated at 70° C. overnight. The reaction mixture was evaporated and the residue partitioned between ether and water. The organic layer was separated, dried and evaporated. The residue was purified by column chromatography on silica gel eluted with hexane and then hexane: dichworomethane (2:1). Combination and evaporation of suitable fractions followed by recrystallisation from hexane gave the title compound as a white solid, m.p. 69.8–70.4° C.

$^1$H NMR (CDCl$_3$) δ: 5.61 (d, 1H), 6.2 (d, 1H), 6.56 (dd, 1H), 7.8 (s, 2H)

MS (thermospray): M/Z[M+NH$_4$]383.1; C$_{13}$H$_5$Cl$_3$F$_3$N$_3$+NH$_4$ requires 382.98.

Example F25 (Illustrative)

5-Chloro-3-cyano-1-(2,6-dichloro-4-trifluoromethylphenyl)-4-formylpyrazole

To a solution of 5-chloro-3-cyano-1-(2,6-dichloro-4-trirluoromethylphenyl)-4-ethenylpyrazole (0.6352 g) in acetone (18 ml) was added water (2 ml), osmium tetroxide (0.57 ml of a 2.5% solution in t-butanol) and sodium metaperiodate (0.749 g). After stirring at room temperature for 1 hour, sodium metaperiodate (0.749 g) was added and stirring continued for 1 hour. The reaction mixture was evaporated and the residue treated with ethyl acetate (20 ml) and aqueous potassium hydrogen carbonate solution (3 ml). After stirring for 20 minutes the layers were separated. The aqueous layer was extracted with ethyl acetate. The combined ethyl acetate extracts were washed with aqueous potassium hydrogen carbonate solution, then brine, dried (Na$_2$SO$_4$) and evaporated. The residue was purified by column chromatography on silica gel eluted with hexane: dichloromethane (2:1). Combination and evaporation of suitable fractions followed by recrystallisation from hexane gave the title compound as a white solid, m.p. 145.2–145.9° C.

$^1$H NMR (CDCl$_3$) δ: 7.84 (s, 2H), 10.04 (s, 1H).

MS (thermospray): M/Z[M+NH$_4$]385.3; C$_{12}$H$_3$Cl$_3$F$_3$N$_3$O+NH$_4$ requires 384.96.

Example F26

5-Chloro-3-cyano-1-(2,6-dichloro-4-trifluoromethylphenyl)4-(2,2-dibromoethenyl)pyrazole To a stirred solution of triphenylphosphine (0.709 g) in dry dichloromethane (2 ml) at 0° C. under an atmosphere of dry nitrogen was added carbon tetrabromide (0.358 g) in dry dichloromethane (2 ml) followed by 5-chloro-3-cyano-1-(2,6-dichloro-4-trifluoromethylphenyl)4-formylpyrazole (0.2 g) in dry dichloromethane (3 ml). The mixture was allowed to warm to room temperature and stirring continued overnight. The reaction mixture was washed with water. The aqueous layer was twice extracted with dichloromethane. The combined organic layers were washed with brine, dried (Na$_2$SO$_4$) and evaporated. The residue was purified by column chromatography on silica get eluted with hexane dichloromethane (1:1). Combination and evaporation of suitable fractions followed by recrystallisation from hexane gave the title compound as a white solid, m.p. 119.1–119.5° C.

$^1$H NMR (CDCl$_3$) δ: 7.24 (s, 1H), 7.81 (s, 2H)

MS (thermospray): M/Z[M+NH$_4$]538.8; C$_{13}$H$_3$Br$_2$Cl$_3$F$_3$N$_3$+NH$_4$ requires 538.81.

Example F27

5-Chloro-3-cyano-1-(2,6-dichloro-4-trifluoromethylphenyl) 4-ethynylpyrazole

To a stirred solution of 5-chloro-3-cyano-)-4-(2,2-dibromoethenyl)-1-(2,6-dichloro-4-trifluoromethylphenyl)

pyrazole (2.12 g) in dimethylsulphoxide (8 ml) at 15° C. was added dropwise a solution of 1,8-diazabicyclo[5.4.0]undec-7-ene (1.21 ml) in dimethylsulphoxide (7.9 ml). After two hours the reaction mixture was neutralism with 0.5N hydrochloric acid and partitioned between water and dichloromethane. The aqueous layer was thrice extracted with dichloromethane. The combined organic layers were washed with brine, dried ($Na_2SO_4$) and evaporated. The aqueous layer was thrice extracted with dichloromethane. The combined organic layers were washed with brine, dried ($Na_2SO_4$) and evaporated. The residue was purified by column chromatography on silica gel eluted with hexane dichloromethane (1:1). Combination and evaporation of suitable fractions followed by recrystallisation from hexane gave the title compound as a light pink solid, m.p. 109.1–109.9° C.

$^1$H NMR ($CDCl_3$) δ: 3.54 (s, 1H), 7.8 (s, 2H)

MS (thermospray): M/Z[M+$NH_4$]380.7; $C_{13}H_3Cl_3F_3N_3$+$NH_4$ requires 380.97.

Example F28
4-Bromoethynyl-5-chloro-3-cyano-1-(2,6-dichloro-4-trifluoromethylphenyl)pyrazole To a stirred solution of 5-chloro-3-cyano-1-(2,6-dichloro-4-trifluoromethylphenyl)4-ethynylpyrazole (0.499 g) in acetone (5 ml) was added N-bromosuccinimide (0.244 g) followed by silver nitrate (0.023 g). Stirring was continued for one hour then the reaction mixture was evaporated to dryness. The residue was partitioned between ether and water. The aqueous layer was separated and extracted with ether. The combined organic layers were washed with brine, dried ($Na_2SO_4$) and evaporated. The residue was purified by column chromatography on silica gel eluted with dichloromethane: hexane (1:1). Combination and evaporation of suitable fractions followed by recrystallisation from hexane provided the title compound as a white solid m.p. 152.9–153.4° C.

$^1$H NMR ($CDCl_3$) δ: 7.80 (s, 2H)

MS (thermospray): M/Z[M+$NH_4$]459.0; $C_{13}H_2BrCl_3F_3N_3$+$NH_4$ requires 458.88.

Example F29
4-(2-bromo-1,2-dichloroethenyl)-5-Chloro-3-cyano-1-(2,6-dichloro-4-trifluoromethylphenyl pyrazole To a stirred solution of 4-bromoethynyl-5-chloro-3-cyano-1-(2,6-dichloro-4-trifluoromethylphenyl)pyrazole (0.42 g) in dichloromethane (10 ml) cooled to −78° C. was added a solution of chlorine (0.134 g) in dichloromethane (5 ml). Stirring was continued at 78° C. for two hours and then the reaction mixture was allowed to warm to room temperature. Stirring was continued overnight then the mixture was evaporated to dryness. The residue was purified by column chromatography on silica gel eluted with dichloromethane: hexane (1:1). Combination and evaporation of suitable fractions followed by recrystallisation from hexane provided the title compound as a white solid m.p. 91.1–91.9° C.

$^1$H NMR ($CDCl_3$) δ: 7.80 (s, 2H)

MS (thermospray): M/Z[M+$NH_4$]528.9; $C_{13}H_2BrCl_5F_3N_3$+$NH_4$ requires 528.81.

Example F30
3-Cyano-1-(2,6-dichloro-4-trifluoromethylphenyl)-4-(1-methylethen-1-yl)pyrazole To a solution of 4-acetyl-3-cyano-1-(2,6-dichloro-4-trifluoromethylphenyl)pyrazole (0.75 g) in tetrahydrofuran (5 ml) cooled to −40° C. under an atmosphere of nitrogen was added μ-chloro-μ-methylene-[bis(cyclopentadienyl)titanium]dimethylaluminium (5.18 ml of a 0.5M solution in toluene) and the mixture was stirred for 15 minutes then allowed to warm to room temperature. After 2 hours at room temperature 0.1M aqueous sodium sulphate solution was added dropwise until effervescence ceased. The reaction mixture was diluted with ether (50 ml), washed with aqueous sodium sulphate solution, dried and evaporated. The residue was purified by column chromatography on silica gel eluted with dichloromethane: hexane (1:1). Combination and evaporation of suitable fractions provided the title compound as a tan solid m.p. 63–64° C.

$^1$H NMR ($CDCl_3$) δ: 2.63 (s, 3H), 5.19 (m, 1H), 5.32 (m, 1H), 7.49 (s, 1H), 7.87 (s, 2H)

MS (thermospray): M/Z[M+$NH_4$]363.0; $C_{14}H_8Cl_2F_3N_3$+$NH_4$ requires 363.04.

Example F31
3-Cyano-1-(2,6-dichloro-4-trifluoromethylphenyl)-4-(2-methylprop-1-enyl)pyrazole Isopropyltriphenylphosphonium iodide (0.97 g) in anhydrous ether (10 ml) was treated at room temperature with n-butyllithium (0.9 ml of a 2.5M solution in hexanes). To the resulting dark red solution was added 3-cyano-1-(2,6-dichloro-4-trifluoromethylphenyl)4-formylpyrazole (0.6 g) in ether (20 ml) and the mixture stirred for 2 hours. The solution was washed with water (20 ml) and the separated organic layer dried ($MgSO_4$) and evaporated. The residue was purified by column chromatography on silica gel eluted with dichloromethane. Combination and evaporation of suitable fractions provided the title compound as a pale tan solid m.p. 72–74° C.

$^1$H NMR ($CDCl_3$) δ: 1.9 (s, 3H), 1.99 (s, 3H), 6.17 (s, 1H), 7.6 (s, 1H), 7.77 (s, 2H)

MS (thermospray): M/Z[M+$NH_4$]360.2; $C_{15}H_{10}Cl_2F_3N_3$+$NH_4$ requires 360.03.

Example G1 (Illustrative)
5-Amino-1-(2,6-dichloro-4-trifluoromethylphenyl)4-iodo-3-trifluoromethylpyrazole To a stirred solution of 5-amino-1-(2,6-dichloro-4-trifluoromethylphenyl)-3-trifluoromethylpyrazole (0.182 g) in acetonitrile (3 ml) at room temperature was added N-iodosuccinimide (0.113 g). After 20 minutes the mixture was evaporated to dryness and the residue taken up in dichloromethane (20 ml). After washing with water (20 ml, ×2), brine (20 ml) and drying ($MgSO_4$) the solution was evaporated. The residue was triturated with hexane and the supernatant evaporated to give the title compound as an off-white solid, m.p. 126° C.

$^1$H NMR ($CDCl_3$) δ: 3.9 (br. s, 2H), 7.80 (s, 2H)

MS (thermospray): M/Z[M+H]490.2; $C_{11}H_4Cl_2F_6IN_3$+H requires 489.88.

Example G2 (Illustrative)
1-(2,6-Dichloro-4-trifluoromethylphenl)-4-iodo-3-trifluoromethylpyrazole To a stirred solution of 5-amino-1-(2,6-dichloro-4-trifluoromethylphenyl)-4-iodo-3-trifluoromethylpyrazole (3.3 g) in tetrahydrofuiran (25 ml) at 65° C. was added dropwise t-butylnitrite (4.22 g) in tetrahydrofuiran (5 ml) over a period of 30 minutes and heating continued for 3 hours. The reaction mixture was evaporated to an oil which solidified on standing. Crystallisation from propan-2-ol gave the title compound as yellow solid, m.p. 109–112° C.

$^1$H NMR ($CDCl_3$) δ: 7.7 (s, 1H), 7.77 (s, 2H)

Microanalysis: C: 27.87, H: 0.69, N: 6.15%; $C_{11}H_4Cl_2F_6IN_3$ requires C: 27.82, H: 0.64, N: 5.90%.

Example G3
1-(2,6-Dichloro-4-trifluoromethylphenyl)-4-ethenyl-3-trifluoromethylpyrazole A solution of 1-(2,6-dichloro-4-trifluoromethylphenyl)-4-iodo-3-trifluoromethylpyrazole (1 g) in dimethylformamide (5 ml) containing vinyltri-n-butyltin (2 ml) and tetrakis(triphenylphosphine)palladium(0) (0.1 g) was stirred at 75° C. for 3 hours. The reaction mixture was evaporated and then partitioned between water and ether. The organic layer was separated, washed with water (×5), dried (Na$_2$SO$_4$) and evaporated. The residue was crystalised from hexane and further purified by column chromatography on silica gel eluted with ether. Combination and evaporation of appropriate fractions gave a yellow solid which was further purified by reverse phase high performance chromatography on C18 silica eluted with acetonitrile: methanol: water (40:10:50). Combination and evaporation of appropriate fractions, followed by recrystallisation from propan-2-ol, gave the title compound as a light yellow solid, m.p.95–98° C.

$^1$H NMR (CDCl$_3$) δ: 5.39 (d, 1H), 5.65 (d, 1H), 6.69 (dd, 1H), 7.8 (s, 1H), 7.81 (s, 2H).

MS (thermospray): M/Z[M+NH$_4$]391.9; C$_{13}$H$_6$Cl$_2$F$_6$N$_2$+NH$_4$ requires 392.02.

Example G4

5-Amino-1-(2,6-dichloro-4-trifluoromethylphenyl)-3-trifluoromethyl-4-trimethylsilylethynylpyrazole To a stirred solution of 5-amino-1-(2,6-dichloro-4-trifluoromethylphenyl)-4-iodo-3-trifluoromethylpyrazole (28 g) in triethylamine (120 ml) and dimethylformamide (24 ml) at room temperature was added trimethylsilylacetylene (12 ml), cuprous iodide (0.6 g) and bis(triphenylphosphine)palladium(II) chloride (1.2 g). The mixture was heated under reflux for 4 hours and then left at room temperature overnight. The reaction mixture was diluted with water (500 ml) and ether (500 ml) and filtered. The filtrate's organic layer was separated, dried (MgSO$_4$) and evaporated to give the crude product as an oil which was purified by column chromatography on silica gel eluted with dichloromethane-:hexane (1:1). Combination and evaporation of appropriate fractions, followed by recrystallisation from hexane, provided the title compound as a buff solid, m.p. 120–123° C.

$^1$H NMR (CDCl$_3$) δ: 0.28 (s, 9H), 4.12 (br. s, 2H), 7.75 (s, 2H).

MS (thermospray): M/Z[M+H]459.9; C$_{16}$H$_{13}$Cl$_2$F$_6$N$_3$Si+H requires 460.02.

Example G5

1-(2,6-Dichloro-4-trifluoromethylphenyl)-3-trifluoromethyl-4-trimethylsilylethynylpyrazole To a stirred solution of 5-amino-1-(2,6-dichloro-4-trifluoromethylphenyl)-3-trifluoromethyl4-trimethylsilylethynylpyrazole (6.39 g) in tetrahydrofuran (50 ml) at 65° C. was added dropwise over one hour t-butylnitrite (7.15 g) in tetrahydrofuran (10 ml). Heating was continued for 2 hours then the mitue was left at room temperature overnight. After evaporation the residue was taken up in hexane and decanted free from insoluble materials. The solution was evaporated and the residue purified by column chromatography on silica gel eluted with dichloromethane:hexane (1:1). Combination and evaporation of appropriate fractions, followed by recrystallisation from hexane, provided the title compound as a pale yellow solid, m.p. 105–108° C.

$^1$H NMR (CDCl$_3$) δ: 0.28 (s, 9H), 7.74 (s, 1H), 7.75 (s, 2H).

MS (thermospray): M/Z[M+NH$_4$]461.8; C$_{16}$H$_{12}$Cl$_2$F$_6$N$_2$Si+NH$_4$ requires 462.04.

Example G6

1-(2,6-Dichloro-4-trifluoromethylphenyl)-4-ethynyl-3-trifluoromethylpyrazole

To a stirred solution of 1-(2,6-dichloro-4-trifluoromethylphenyl)-3-trifluoromethyl4-trinmethylsilylethynylpyrazole (4.6 g) in methanol (75 ml) was added potassium carbonate (2.5 g). After 3 hours at room temperature the reaction mixture was concentrated and then partitioned between ether (250 ml) and water (250 ml). The organic layer was separated, washed with brine, dried and evaporated to give an oil which was crystallised from hexane to provide the title compound as a pale yellow solid m.p. 95–98° C.

$^1$H NMR (CDCl$_3$) δ: 3.27 (s, 1H), 7.75 (s, 2H), 7.79 (s, 1H)

MS (thermospray): M/Z[M+NH$_4$]390.2; C$_{13}$H$_4$Cl$_2$F$_6$N$_2$+NH$_4$ requires 390.0.

Example G7

4-Bromoethynyl-1-(2,6-dichloro-4-trifluoromethylphenyl)-3-trifluoromethylpyrazole To a stirred solution of 1-(2,6-dichloro-4-trifluoromethylphenyl)4ethynyl-3-trifluoromethylpyrazole (3.1 g) in acetone (25 ml) was added N-bromosuccinimide (1.4 g) and silver nitrate (0. 14 g). Stirring was continued at room temperature for 2 hours. The reaction mixture was evaporated and the residue partitioned between ether and water. The organic layer was separated, dried and evaporated. The residue was purified by column chromatography on silica gel (10 g) eluted with hexane and then dichloromethane: hexane (1:1). Combination and evaporation of appropriate fractions, followed by crystallisation from hexane, gave the title compound as a white solid m.p. 92–94° C.

$^1$H NMR (CDCl$_3$) δ: 7.77 (s, 1H), 7.78 (s, 2H)

MS (thermospray): M/Z[M+NH$_4$]468.6; C$_{13}$H$_3$BrCl$_2$F$_6$N$_2$+NH$_4$ requires 468.91.

Example G8

4-(2-Bromo-1,2-dichloroethenyl)-1-(2,6-dichloro-4-trifuoromethylphenyl)-3-trifluoromethylpyrazole To a stirred solution of 4-bromoethynyl-1-(2,6-dichloro-4-trifluoromethylphenyl)-3-trifluoromethylpyrazole (0.45 g) in dichloromethane (10 ml) at −78° C. was added dropwise a solution of chlorine (0.142 g) in dichloromethane (5 ml). The mixture was stirred at −78° C. for 2 hours and then allowed to warm to room temperature overnight. The mixture was evaporated and the residue was purified by column chromatography on silica gel (10 g) eluted with hexane and then dichloromethane: hexane (1:1). Combination and evaporation of appropriate fractions, followed by crystallisation from hexane, gave the title compound as a light yellow solid m.p. 57–59° C.

$^1$H NMR (CDCl$_3$) δ: 7.77 (s, 1H), 7.79 (s, 2H)

Microanalysis: Found: C: 30.14, H: 0.55, N: 6.67%; C$_{13}$H$_3$BrCl$_4$F$_6$N$_2$ requires C: 29.86, H: 0.58, N: 5.36%.

Example G9 (Illustrative)

1-(2,6-Dichloro-4-trifluoromethylphenyl)-3,5-dimethyl-4-iodopyrazole

To a stirred solution of 1-(2,6-dichloro-4-trifluoromethylphenyl)-3,5-dimethylpyrazole (0.218 g) in acetonitrile (3 ml) at room temperature was added dropwise a solution of N-iodosuccinimide (0.158 g) in acetonitrile (2 ml). After 27 hours the mixture was evaporated to dryness and the residue purified by column chromatography on silica gel (5 g) eluted with dichloromethane. Combination and evaporation of suitable fractions provided the title compound as yellow oil.

$^1$H NMR (CDCl$_3$) δ: 2.11 (s, 3H), 2.32 (s, 3H), 7.73 (s, 2H)

MS (thermospray): M/Z[M+H]435.0; $C_{12}H_8Cl_2F_3IN_2$+H requires 434.91.

Example G10
1-(2,6-Dichloro-4-trifluoromethylphenyl)-3,5-dimethyl-4-ethenylpyrazole A solution of 1-(2,6-dichloro-4-trifluoromethylphenyl)-3,5-dimethyl4-iodopyrazole (1 g) in dimethylformamide (10 ml) containing vinyltri-n-butyltin (2 ml) and tetrakis (triphenylphosphine)palladium(0) (0.1 g) was stirred at 75° C. for 2 hours then left overnight at room temperature. The mixture was again heated at 75° C. for 2 hours then vinyltri-n-butyltin (2 ml) was added and the mixture heated at 75° C. for 2 hours. Tetrakis(triphenylphosphine)palladium (0) (0.1 g) was added and heating continued for a further 2 hours. The reaction mixture was evaporated and the residue partitioned between water and dichloromethane. The organic layer was separated, washed with water (x2), then brine, dried ($Na_2SO_4$) and evaporated. The residue was adsorbed onto silica gel (20 g) and purified by column chromatography on silica gel (150 g) eluted with hexane, then hexane with increasing amounts of dichloromethane and finally dichloromethane. Combination and evaporation of suitable fractions provided the title compound as yellow oil.

$^1$H NMR (CDCl$_3$) δ: 2.11 (s, 3H), 2.4 (s, 3H), 5.23 (d, 1H), 5.41 (d, 1H), 6.59 (dd, 1H), 7.71 (s, 2H).

MS (thermospray): M/Z[M+H]335.1; $C_{14}H_{11}Cl_2F_3N_2$+H requires 335.03.

Example G11 (Illustrative)
5-Amino-1-(2,6-dichloro-4-trifluoromethylphenyl)4-iodo-3-methylpyrazole To a stirred solution of 5-amino-1-(2,6-dichloro-4-trifluoromethylphenyl)-3-methyl pyrazole (9 g) in acetonitrile (200 ml) at room temperature was added N-iodosuccinimide (5.5 g). The mixture was heated under reflux for one hour and then left at room temperature overnight. The mixture was evaporated and the residue was triturated with hot hexane. The precipitate obtained upon cooling was filtered off and dried to give the title compound as an off-white solid, m.p. 116–118° C.

$^1$H NMR (CDCl$_3$) δ: 2,24 (s, 3H), 3.68 (br. s, 2H), 7.74 (s, 2H)

MS (thermospray): M/Z[M+H]435.8; $C_{11}H_7Cl_2F_3IN_3$+H requires 435.91.

Example G12 (Illustrative)
1-(2,6-Dichloro-4-trifluoromethlphenyl)-4-iodo-3-methylpyrazole To a stirred solution of 5-amino -1-(2,6-dichloro-4-trifluoromethylphenyl)-4-iodo-3-methylpyrazole (2.85 g) in tetrahydrofuran (35 ml) at 0° C. was added dropwise t-butylnitrite (2.33 ml). The reaction mixture was allowed to warm to room temperature and then heated under reflux for 1.5 hours. The reaction mixture was evaporated and the residue purified by column chromatography on silica gel eluted with dichloromethane: hexane (1:1). Combination and evaporation of suitable fractions provided a yellow oil which was further purified by column chromatography on silica gel eluted with dichloromethane: hexane (1:2). Combination and evaporation of suitable fractions provided the title compound as a white solid, m.p. 118.5–119.4° C.

$^1$H NMR (CDCl$_3$) δ: 2.18 (s, 3H), 7.54 (s, 1H), 7.7 (s, 2H)

MS (thermospray): MZ[M+H]420.5 ; $C_{11}H_6Cl_2F_3IN_2$+H requires 419.89.

Example G13
1-(2,6-Dichloro-4-trifluoromethylphenyl)-4-ethenyl-3-methylpyrazole To a stirred solution of 1-(2,6-dichloro-4-trifluoromethylphenyl)4-iodo-3-methylpyrazole (2.06 g) in dimethylformamide (25 ml) was added tetrakis (triphenylphosphine)palladium(0) (0.1 g) and vinyltri-n-butyltin (2 ml). The mixture was heated at 70° C. for 2 hours. The reaction mixture was evaporated and then partitioned between water and ether. The aqueous layer was separated and extracted twice with ether. The combined organic layers were washed with brine, dried ($Na_2SO_4$) and evaporated. The residue was purified by column chromatigraphy on silica gel eluted with hexane: ether (9:1). Combination and evaporation of appropriate fractions gave a yellow solid which was further purified by reverse phase high performance chromatography on C18 silica eluted with acetonitrile: methanol: water (40:10:50). Combination and evaporation of appropriate fractions gave the title compound as a white solid, m.p.68.1–68.7° C.

$^1$H NMR (CDCl$_3$) δ: 2.44 (s, 3H), 5.24 (d, 1H), 5.5 (d, 1H), 6.62 (dd, 1H), 7.57 (s, 1H),7.74 (s, 2H).

MS (thermospray): M/Z[M+H]321.1; $C_{13}H_9Cl_2F_3N_2$+H requires 321.02.

Example G14
5-Amino-1-(2,6-dichloro-4-trifluoromethylphenyl)-3-methyl4-trimethylsilylethynylpyrazole To a stirred solution of 5-amino-1-(2,6-dichloro-4-trirluoromethylphenyl)-4-iodo-3-methylpyrazole (9.lg) in triethylamine (45 ml) and dimethylformamide (9 ml) at room temperature was added trimethylsilylacetylene (4.5 ml), cuprous iodide (0.225 g) and bis(triphenylphosphine)palladium(II) chloride (0.45 g). The mixture was heated under reflux for 4 hours and the left at room temperature overnight. The reaction mixture was evaporated to give the crude product as an oil which was purified by column chromatography on silica gel eluted with dichioromethane-:hexane (1:1). Combination and evaporation of appropriate fractions, followed by recrystallisation from hexane, provided the title compound as a buff solid, m.p. 121–123° C.

$^1$H NMR (CDCl$_3$) δ: 0.28 (s, 9H), 2.3 (s, 3H), 3.92 (br. s, 2H), 7.82 (s, 2H).

MS (thermospray): M/Z[M+H]406.0; $C_{16}H_{16}Cl_2F_3N_3Si$+H requires 406.05.

Example G15
1-(2,6-Dichloro-4-trifluoromethylphenyl)-3-methyl-4-trimethylsilylethynylpyrazole To a stirred solution of 5-amino-1-(2,6-dichloro-4-trifluoromethylphenyl)-3-methyl 4-trimethylsilylethynylpyrazole (1.3 g) in tetrahydrofuran (15 ml) at 65° C. was added dropwise t-butylnitrite (1.65 g) in tetrahydrofuran (5 ml) over a period of 15 minutes and heating continued for 3 hours. The reaction mixture was left at room temperature overnight then evaporated to give the crude product as a gum which was purified by column chromatography on silica gel eluted with dichioromethane-:hexane (1:1). Combination and evaporation of appropriate fractions provided the title compound as a pale yellow solid, m.p. 76–78° C.

$^1$H NMR (CDCl$_3$) δ: 0.28 (s, 9H), 2.43 (s, 3H), 7.62 (s, 1H), 7.72 (s, 2H)

MS (thermospray): M/Z[M+H]391.0; $C_{16}H_{15}Cl_2F_3N_2Si$+H requires 391.04.

Example G16
1-(2,6-dichloro-4-trifluoromethylphenyl)-4-ethynyl-3-methylpyrazole To a stirred solution of 1-(2,6-dichloro-4-trifluoromethylphenyl)-3-methyl4- trimethylsilylethynylpyrazole (0.82 g) in methanol (15 ml) was added potassium carbonate (0.75 g). After 3 hours at room temperature the reaction mixture was poured into water (100 ml) and extracted with ether (50 ml, ×2). The combined organic layers were washed with brine, dried and evaporated to provide the title compound as a light beige gum.

$^1$H NMR (CDCl$_3$) δ: 2.45 (s, 3H), 3.21 (s, 1H), 7.64 (s, 1H), 7.81 (s, 2H)

MS (thermospray): M/Z[M+H]319.0 ; C$_{13}$H$_7$Cl$_2$F$_3$N$_2$+H requires 319.0.

Example G17
4-Bromoethynyl-1-(2,6-dichloro-4-trifluoromethylphenyl)-3-methylpyrazole To a stirred solution of 1-(2,6-dichloro-4-trifluoromethylphenyl)4-ethynyl-3-methylpyrazole (0.53 g) in acetone (5 ml) was added N-bromosuccinimide (0.295 g) and silver nitrate (0.028 g). Stirring was continued at room temperature for 1 hour. The reaction mixture was evaporated and the residue taken up in ether and washed with water. The organic layer was separated, dried and evaporated. The residue was purified by column chromatography on silica gel (10 g) eluted with hexane and then dichloromethane: hexane (1:1). Combination and evaporation of appropriate fractions, followed by crystailisation from hexane, gave the title compound as a very pale yellow solid m.p. 86–89° C.

$^1$H NMR (CDCl$_3$) δ: 2.42 (s, 3H), 7.62 (s, 1H), 7.81 (s, 2H)

Microanalysis: Found: C: 39.20, H: 1.52, N: 6.94%; C$_{13}$H$_6$BrCl$_4$F$_3$N$_2$ requires C: 39.23, H: 1.52, N: 7.04%.

Example G18 (Illustrative)
5-Amino-1-(2,6-dichloro-4-trifluoromethylphenyl)-3-phenylpyrazole A solution of 2,6-dichloro-4-trifluoromethylphenylhydrazine (0.245 g) in ethanol (2 ml) was added to benzoylacetonitrile (0. 145 g) in ethanol (8 ml) and the solution heated at 80° C. for 6 hours. Glacial acetic acid (1 ml) was added and the mixture heated at 80° C. for 4 hours and then 90° C. for 2 hours. The reaction mixture was evaporated and the residue purified by column chromatography on silica gel (10 g) eluted with dichloromethane. Combination and evaporation of appropriate fractions followed by further purification of their residue by reverse phase high performance liquid chromatography on C18 silica eluted with methanol: acetonitrile: water (1:5:4). Combination and evaporation of appropriate fractions gave the title compound as a white solid m.p. 141.5–142.5° C.

$^1$H NMR (CDCl$_3$) δ: 3.60 (br. s, 2H), 6.08 (s, 1H), 7.3–7.45 (m, 3H), 7.80 (s, 2H), 7.8–7.85 (m, 2H)

MS (thermospray): M/Z[M+H]372.1; C$_{16}$H$_{10}$Cl$_2$F$_3$N$_2$+H requires 372.03.

Example G19 (Illustrative)
5-Amino-1-(2,6-dichloro-4-trifluoromethylphenyl)4-iodo-3-phenylpyrazole To a stirred solution of 5-amino-1-(2,6-dichloro-4-trifluoromethylphenyl)-3-phenylpyrazole (0.12 g) and N-iodosuccinirnide (0.08 g) in acetonitrile (5 ml) were left at room temperature overnight. The mixture was evaporated to dryness and the residue partitioned between dichloromethane (15 ml) and water (10 ml). The organic layer was separated and washed with water (20 ml, ×2), brine (15 ml) and dried (MgSO$_4$) and evaporated. The residue was triturated with hexane to give the title compound as a yellow solid, m.p. 162–164° C.

$^1$H NMR (CDCl$_3$) δ: 3.8 (br. s, 2H), 7.35 (m, 3H), 7.78 (s, 2H), 7.95 (m, 2H)

MS (thermospray): M/Z[M+H]498.1; C$_{16}$H$_9$Cl$_2$F$_3$IN$_3$+H requires 497.93.

Example G20 (Illustrative)
1-(2,6-Dichloro-4-trifluoromethylphenyl)-4-iodo-3-phenylpyrazole To a stirred solution of 5-amino-1-(2,6-dichloro-4-trifluoromethylphenyl)4iodo-3-phenylpyrazole (2.5 g) in tetrahydrofuiran (50 ml) at 65° C. was added dropwise t-butylnitrite (3 g) in tetrahydrofuran (20 ml) over a period of 30 minutes and heating continued for 3 hours then left at room temperature overnight. The reaction mixture was evaporated to an oil which was purified by column chromatography on silica gel eluted with dichloromethane. Combination and evaporation of appropriate fractions, followed by further column chromatography on silica gel eluted with hexane, then hexane containing 5% ethyl acetate and finally hexane containing 10% ethyl acetate. Combination and evaporation of appropriate fractions gave the title compound as a cream solid m.p. 88–89° C.

$^1$H NMR (CDCl$_3$) δ: 7.45 (m, 3H), 7.7 (s, 1H), 7.72 (s, 2H), 7.95 (m, 2H)

MS (thermospray): M/Z[M+H]482.8; C$_{16}$H$_8$Cl$_2$F$_3$IN$_2$+H requires 482.91.

Example G21
1-(2,6-Dichloro-4-trifluoromethylphenyl)4-ethenyl-3-phenyl-pyrazole A solution of 1-(2,6-dichloro-4-trifluoromethylphenyl)-4-iodo-3-phenylpyrazole (1 g) in dimethylformamide (12 ml) was added tetrakis(triphenylphosphine)palladium(0) (0.07 g) and the mixture stirred at room temperature for 10 minutes. Vinyltri-n-butyltin (1.8 ml) was added and the mixture heated at 70° C. for 6 hours and then left at room temperature overnight. The reaction mixture was evaporated and then partitioned between water (50 ml) and dichloromethane (50 ml). The organic layer was separated, dried (MgSO$_4$) and evaporated. The residue was purified by column chromatography on silica gel eluted with hexane containing increasing amounts of ethyl acetate. Appropriate fractions were combined and evaporated and their residue was further purified by column chromatography on silica gel eluted with hexane containing amounts of ether. Combination and evaporation of appropriate fractions gave the title compound as a yellow oil.

$^1$H NMR (CDCl$_3$) δ: 5.25 (d, 1H), 5.65 (d, 1H), 6.80 (dd, 1H), 7.45 (m, 3H), 7.75 (m, 5H),

MS (thermospray): M/Z[M+H]383.3; C$_{18}$H$_{11}$Cl$_2$F$_3$N$_2$+H requires 383.03.

PREPARATIONS

Preparation 1:5-Amino-3-cyano-1-(2,6-dichloro-4-trifluoromethylphenyl)pyrazole, used in example A1, was prepared as described in EP-295,117.

Preparation 2:5-Amino-3-cyano-1-(2,6-dichloro-4-trifluoromethoxyphenyl)pyrazole, used in example D1, was prepared as described in EP-295,117.

Preparation 3:5-Amino-3-cyano-1-(2,6-dichloro-4-trifluoromethylsulphenylphenyl)-pyrazole, used in example D7, was prepared by adaptation of the method mentioned above re. Preparation 2.

Preparation 4:5-Amino-3-cyano-1-(2,6-dichloro-4-sulphurpentafluorophenyl)pyrazole, used in example D11, was prepared as described in WO 93/06089.

Preparation 5:5-Amino-1-(2,6-dichloro-4trifluoromethylphenyl)-3-trifluoromethylpyrazole, used in example G1, was prepared as described in WO 87/03781.

Preparation 6:1-(2,6-Dichloro-4-trifluoromethylphenyl)-3,5-dimethylpyrazole, used in example G9, was prepared as described in Can. J. Chem.,1979, 57, 904.

Preparation 7:5-Amino-1-(2,6-dichloro-4-trifluoromethylphenyl)-3-methylpyrazole, used in example G11, was prepared by adaptation of the method described in DE 4414333 for the preparation of 5-amino-1-[(3-chloro-5-trifluoromethyl)-2-pyridyl]-3-methyl-pyrazole.

Biological Test Result

The compound of Example A3 was found to produce 100% mortality in the dosage range 0.005–100 μg per fly, using the test method described earlier.

What is claimed is:

1. A compound of formula I,

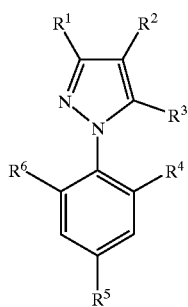

wherein $R^1$ represents CN, $C_{1-6}$ alkoxycarbonyl, $NO_2$, CHO, $C_{1-6}$ alkanoyl, phenyl optionally substituted by one or more halogen, or $C_{1-6}$ alkyl optionally substituted by one or more halogen;

$R^2$ represents a group of formula II, III or IV,

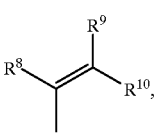

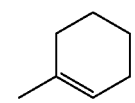

in which $R^7$ represents H, halogen, carbamoyl, cyano, tri($C_{1-6}$ alkyl)silyl, $C_{1-6}$ alkyl optionally substituted by one or more halogen, OH or $C_{1-6}$ alkoxy, $C_{1-6}$ alkoxycarbonyl, phenyl, or a 5- or 6-membered ring heterocycle which is saturated or partially or fully unsaturated and contains up to 4 hetero-atoms independently selected from up to 4 N atoms, up to 2 O atoms and up to 2 S atoms and which is attached to the alkynyl moiety by an available C, S or N atom where the valence allows;

and $R^8$, $R^9$ and $R^{10}$ each independently represent H, halogen, phenyl optionally substituted by one or more halogen, CN or $C_{1-6}$ alkyl optionally substituted by one or more halogen; $R^3$ represents H, $C_{1-6}$ alkyl, halogen, $NH_2$, $NH(C_{1-6}$ alkanoyl), $NH(C_{1-6}$ alkoxycarbonyl), $N(C_{1-6}$ alkoxycarbonyl)$_2$, $NH(C_{1-6}$ alkyl), $N(C_{1-6}$ alkyl)$_2$, $NHCONH(C_{1-6}$ alkyl), N-pyrrolyl, NHCONH phenyl wherein the phenyl ring may be optionally substituted by one or more halogen, N=CH(phenyl), OH, $C_{1-6}$ alkoxy, SH or $S(O)_n$ $C_{1-6}$ alkyl wherein the alkyl group may be optionally substituted by one or more halogen) where n is 0, 1 or 2; and $R^4$, $R^5$ and $R^6$ each independently represent H, halogen, $C_{1-6}$ alkyl optionally substituted by one or more halogen, $C_{1-6}$ alkoxy optionally substituted by one or more halogen, $S(O)_n(C_{1-6}$ alkyl optionally substituted by one or more halogen) where n is 0, 1 or 2, or $CH_3CO$, CN $CONH_2$, $CSNH_2$, $OCF_3$, $SCF_3$ or $SF_5$; with the proviso that when $R^4$ and $R^6$ are H, then $R^5$ is not H;

or a pharmaceutically or veterinarily acceptable salt thereof.

2. A compound or salt according to claim 1, where $R^1$ is CN, optionally substituted phenyl, optionally substituted $C_{1-6}$ alkyl, or $C_{1-6}$ alkoxycarbonyl.

3. A compound or salt according to claim 1, where $R^2$ is a group of formula II where $R^7$ is H, tri($C_{1-6}$ alkyt)silyl, $C_{1-6}$ alkyl optionally substituted by one or more halogen, OH or $C_{1-6}$ alkoxy, or $R^7$ is $C_{1-6}$ alkoxycarbonyl, phenyl, a 5- or 6-membered ring heterocycle as previously defined, halogen, or $R^2$ is a group of formula III in which either $R^8$, $R^9$, and $R^{10}$ are each H, or a group of formula III in which two of $R^8$, $R^9$ and $R^{10}$ are halogen and the other is H, CN, phenyl optionally substituted by one or more halogen or $C_{1-6}$ alkyl optionally substituted by one or more halogen, or a group of formula III in which $R^8$, $R^9$ and $R^{10}$ are each independently F, Cl, Br or I, or a group of formula III in which $R^8$ is H or $C_{1-6}$ alkyl optionally substituted by one or more halogen, OH or $C_{1-6}$ alkoxy, and $R^9$ and $R^{10}$ are both halogen, or a group of formula III in which $R^8$ is H and one of $R^9$ and $R^{10}$ is halogen and the other is $C_{1-6}$ alkyl optionally substituted by one or more halogen, OH or $C_{1-6}$ alkoxy, or a group of formula III in which $R^8$ is H and one of $R^9$ and $R^{10}$ is H and the other is CN or $C_{1-6}$ alkyl optionally substituted by one or more halogen, OH or $C_{1-6}$ alkoxy, or a group of formula III in which $R^8$ is H and $R^9$ and $R^{10}$ are $C_{1-6}$ alkyl optionally substituted by one or more halogen, OH or $C_{1-6}$ alkoxy, or a group of formula III in which $R^8$ is $C_{1-6}$ alkyl optionally substituted by one or more halogen, OH or $C_{1-6}$ alkoxy and $R^9$ and $R^{10}$ are both H, or a group of formula IV.

4. A compound or salt according to claim 1, where $R^3$ is H, $C_{1-6}$ alkyl $NH_2$, $NH(C_{1-6}$ alkanoyl), $NH(C_{1-6}$ alkoxycarbonyl), $N(C_{1-6}$ alkoxycarbonyl)$_2$, $N(C_{1-6}$ alkyl)$_2$, N-pyrrolyl, halogen or $S(O)_n(C_{1-6}$ alkyl optionally substituted by one or more halogen) where n is 0,1 or 2.

5. A compound or salt according to claim 1, where $R^4$ and $R^6$ are halogen.

6. A compound or salt according to claim 1, where $R^5$ is $C_{1-6}$ alkyl optionally substituted by one or more halogen, $C_{1-6}$ alkoxy optionally substituted by one or more halogen, $C_{1-6}$ alkylthio optionally substituted by one or more halogen, $SF_5$ or halogen.

7. A compound or salt according to claim 1, where $R^1$ is CN, Ph, $CO_2C_2H_5$, $CH_3$, $CF_3$ or $CO_2CH_3$.

8. A compound or salt according to claim 1, where $R^2$ is a group of formula II in which $R^7$ is $Si(CH_3)_3$, H, $CH_3$, $CH(CH_3)_2$, $CH_2OH$, $(CH_2)_2OH$, $CO_2CH_3$, Ph, thien-2-yl, $CH_2OCH_3$, Br, Cl, or $CF_3$, or a group of formula III in which $R^8$, $R^9$ and $R^{10}$ are each H, or a group of formula III in which $R^8$, $R^9$ and $R^{10}$ are each Cl, or a group of formula III in which $R^8$ and $R^9$ are Br and $R^{10}$ is H, or a group of formula III in which $R^8$ and $R^{10}$ are Br and $R^9$ is H, or a group of formula III in which $R^8$ and $R^9$ are Br and $R^{10}$ is $CH_3$, or a group of formula III in which $R^8$ and $R^{10}$ are Br and $R^9$ is $CH_3$, or a group of formula III in which $R^8$ and $R^{10}$ are Br and $R^9$ is Ph, or a group of formula III in which $R^8$ and $R^9$ are Br and $R^{10}$ is Ph, or a group of formula III in which $R^8$ and $R^{10}$ are Cl and $R^9$ is Ph, or a group of formula III in which $R^8$ and $R^9$ are Cl and $R^{10}$ is Ph, or a group of formula III in which $R^8$ and $R^{10}$ are Cl and $R^9$ is Br, or a group of formula III in which $R^8$ and $R^9$ are Cl and $R^{10}$ is Br, or a group of formula III in which $R^8$ is H and $R^{10}$ and $R^9$ are Br, or a group of formula III in which $R^8$ is H and $R^{10}$ and $R^9$ are Cl, or a group of formula III in which $R^8$ is H and $R^{10}$ and $R^9$ are F, or a group of formula III in which $R^8$ is H and $R^{10}$ is $CF_3$ and $R^9$ is Cl, or a group of formula III in which $R^8$ is H and $R^9$ is $CF_3$ and $R^{10}$ is Cl, or a group of formula III in which $R^8$ is H and $R^{10}$ is $CF_3$ and $R^9$ is Br, or a group of formula III in which $R^8$ is H and $R^9$ is $CF_3$ and $R^{10}$ is Br, or a group of formula III in which $R^8$ is H and $R^{10}$ is $CF_3$ and $R^9$ is F, or a group of formula III in which $R^8$ is H and $R^9$ is $CF_3$ and $R^{10}$ is F, or a group of formula III in which $R^8$ and $R^{10}$ are H and $R^9$ is CN, or a group of formula III in which $R^8$ and $R^9$ are Br and $R^{10}$ is $CF_3$, or a group of formula III in which $R^8$ and $R^{10}$ are Br and $R^9$ is $CF_3$, or a group of formula III in which $R^8$ is Br, $R^9$ is Br and $R^{10}$ is Cl, or a group of formula III in which $R^8$ is Br, $R^{10}$ is Br and $R^9$ is Cl, or a group of formula III in which $R^8$ is $CH_3$, $R^9$ and $R^{10}$ are Br, or a group of formula III in which $R^8$ is $CH_3$, $R^9$ and $R^{10}$ are F, or a group of formula III in which $R^8$ is $CH_3$, $R^9$ and $R^{10}$ are H, or a group of formula III in which $R^8$ is H, $R^9$ and $R^{10}$ are $CH_3$, or a group of formula III in which $R^8$, $R^9$ and $R^{10}$ are each Br, or a group of formula IV.

9. A compound or salt according to claim 1, where $R^3$ is H, $CH_3$, $NH_2$, N-pyrrolyl, $N(CH_3)_2$, $NH(CO_2(t\text{-butyl}))$, $N(CO_2(t\text{-butyl}))_2$, $NHCOCH_3$, Br, Cl, $SCH_3$ or $SCF_3$.

10. A compound or salt according to claim 1, where $R^4$ and $R^6$ are Cl.

11. A compound or salt according to claim 1, where $R^5$ is $CF_3$, $OCF_3$, $SCF_3$ or $SF_5$.

12. A compound or salt thereof according to claim 1, which is selected from:

3-cyano-1-(2,6-dichloro-4-trifluoromethylphenyl)-4-ethynylpyrazole;

3-cyano-1-(2,6-dichloro-4-trifluoromethoxyphenyl)-4-ethynylpyrazole;

3-cyano-1-(2,6-dichloro-4-trifluoromethylsulphenylphenyl)-4-ethynylpyrazole;

4-(2-bromo-1,2-dichloroethenyl)-3-cyano-1-(2,6-dichloro-4-trifluoromethoxyphenyl)-pyrazole;

3-cyano-1-(2,6-dichloro-4-trifluoromethoxyhenyl)-4-tribromoethenylpyrazole;

4-(2,2-dibromoethenyl)-3-cyano-1-(2,6-dichloro-4-trifluoromethylphenyl)-pyrazole;

3-cyano-4-(2,2-dichloroethenyl)-1-(2,6-dichloro-4-trifluoromethylphenyl)pyrazole, 3-cyano-1-(2,6-dichloro-4-trifluoromethylphenyl)-4-(2,2-difluoroethenyl)pyrazole;

3-cyano1-(2,6-dichloro-4-trifluoromethylphenyl)-4-tribromoethenylpyrazole;

3-cyano-1-(2,6-dichloro-4-trifluoromethylphenyl)-4-trichloroethenylpyrazole;

4-(2-bromo-1,2-dichloroethenyl)-3-cyano-1-(2,6-dichloro-4-trifluoromethylphenyl)-pyrazole;

4-(2-chloro-1,2-dibromoethenyl)-3-cyano-1-(2,6-dichloro-4-trifluoromethylphenyl)-pyrazole;

3-cyano-1-(2,6-dichloro-4-trifluoromethylphenyl)-4-(1-methyl-2,2-dibromoethenyl)pyrazole;

3-cyano1-(2,6-dichloro-4-trifiluoromethylphenyl)-4-(1-methyl-2,2-difluoroethenyl)pyrazole;

1-(2,6-dichloro-4-trifluoromethylphenyl)-4-ethynyl-3-trifluoromethylpyrazole;

4-(2-bromo-1,2-dichloroethenyl)-1-(2,6-dichloro-4-trifluoromethylphenyl)-3-trifluoromethylpyrazole; and 1-(2,6-dichloro-4-trifluoromethylphenyl)-4-ethynyl-3-methylpyrazole, or salt thereof.

13. A method of treating a parasitic infestation at a locus, which comprises treatment of the locus with an effective amount of a compound, salt or formulation thereof as defined in claim 1.

14. A method as claimed in claim 13, wherein the locus is the skin or fur of an animal.

15. A method as claimed in claim 13, wherein the locus is a plant or seed.

16. A method of treating a parasitic infestation in a patient which comprises administering an effective amount of a compound or salt as defined in claim 1, to the patient.

17. A method of harming or killing a parasite which comprises administering to said parasite or the locus thereof an effective amount of a compound of the formula (I), or salt or formulation thereof, as claimed in claim 1.

* * * * *